United States Patent
Muller et al.

(10) Patent No.: US 8,469,952 B2
(45) Date of Patent: Jun. 25, 2013

(54) SYSTEM AND METHOD FOR POSITIONING AN EYE THERAPY DEVICE

(75) Inventors: David Muller, Boston, MA (US); Vance Thompson, Sioux Falls, SD (US)

(73) Assignee: Avedro, Inc., Waltham, MA (US)

( * ) Notice: Subject to any disclaimer, the term of this patent is extended or adjusted under 35 U.S.C. 154(b) by 1017 days.

(21) Appl. No.: 12/018,450

(22) Filed: Jan. 23, 2008

(65) Prior Publication Data
US 2009/0187178 A1 Jul. 23, 2009

(51) Int. Cl.
*A61B 18/14* (2006.01)

(52) U.S. Cl.
USPC .......................................................... 606/41

(58) Field of Classification Search
USPC ................. 606/3–7, 10–20, 27–41, 107, 130, 606/166; 604/20; 607/53; 198/898
See application file for complete search history.

(56) References Cited

U.S. PATENT DOCUMENTS

| | | | |
|---|---|---|---|
| 3,073,310 A * | 1/1963 | Mocarski | 606/130 |
| 3,776,230 A | 12/1973 | Neefe | |
| 4,326,529 A | 4/1982 | Doss et al. | |
| 4,381,007 A | 4/1983 | Doss | |
| 4,429,960 A | 2/1984 | Mocilac et al. | 351/212 |
| 4,490,022 A | 12/1984 | Reynolds | |
| 4,712,543 A | 12/1987 | Baron | |
| 4,743,725 A | 5/1988 | Risman | |
| 4,796,623 A | 1/1989 | Krasner et al. | |
| 4,805,616 A | 2/1989 | Pao | |
| 4,881,543 A | 11/1989 | Trembly et al. | |
| 4,891,043 A | 1/1990 | Zeimer et al. | |
| 4,943,296 A * | 7/1990 | Funakubo et al. | 606/166 |
| 4,994,058 A | 2/1991 | Raven et al. | |
| 5,103,005 A | 4/1992 | Gyure et al. | |
| 5,171,254 A | 12/1992 | Sher | |
| 5,281,211 A | 1/1994 | Parel et al. | |
| 5,332,802 A | 7/1994 | Kelman et al. | |
| 5,368,604 A | 11/1994 | Kilmer et al. | 606/166 |
| 5,370,644 A | 12/1994 | Langberg | |

(Continued)

FOREIGN PATENT DOCUMENTS

| | | |
|---|---|---|
| EP | 1 561 440 | 8/2005 |
| EP | 1 790 383 | 5/2007 |

(Continued)

OTHER PUBLICATIONS

International Search Report PCT/US09/31716, dated Feb. 24, 2009.

(Continued)

*Primary Examiner* — Michael Peffley
*Assistant Examiner* — Khadijeh Vahdat
(74) *Attorney, Agent, or Firm* — Nixon Peabody LLP

(57) ABSTRACT

A system for aligning an eye therapy instrument over a selected area or feature of an eye provides an attachment element that is removably attached to a surface of an eye. A receiving element is coupled to the attachment element and movable relative to the attachment element. The receiving element includes a coupling element configured to operably couple an eye therapy instrument to the receiving element and adjustably move the eye therapy instrument into a selected position with respect to the attachment element. The system makes adjustments to ensure accurate delivery of treatment from the eye therapy device to areas of the eye. In one embodiment, the receiving element allows lateral adjustments to be made along one or more axes. Additionally or alternatively, the receiving element allows angular or rotational adjustments to be made about one or more axes.

13 Claims, 13 Drawing Sheets

U.S. PATENT DOCUMENTS

| | | | |
|---|---|---|---|
| 5,395,385 A * | 3/1995 | Kilmer et al. | 606/166 |
| 5,437,658 A | 8/1995 | Muller et al. | |
| 5,461,212 A | 10/1995 | Seiler et al. | |
| 5,490,849 A | 2/1996 | Smith | |
| 5,586,134 A | 12/1996 | Das et al. | |
| 5,591,185 A * | 1/1997 | Kilmer et al. | 606/166 |
| 5,618,284 A | 4/1997 | Sand | |
| 5,624,456 A * | 4/1997 | Hellenkamp | 606/166 |
| 5,626,595 A * | 5/1997 | Sklar et al. | 606/170 |
| 5,634,921 A | 6/1997 | Hood et al. | |
| 5,658,278 A | 8/1997 | Imran et al. | |
| 5,766,171 A | 6/1998 | Silvestrini | |
| 5,779,696 A | 7/1998 | Berry et al. | |
| 5,814,040 A | 9/1998 | Nelson et al. | |
| 5,830,139 A | 11/1998 | Abreu | |
| 5,873,901 A | 2/1999 | Wu et al. | |
| 5,885,275 A | 3/1999 | Muller | |
| 5,910,110 A | 6/1999 | Bastable | |
| 5,919,222 A | 7/1999 | Hjelle et al. | |
| 5,938,674 A | 8/1999 | Terry | 606/166 |
| 6,033,396 A | 3/2000 | Huang et al. | |
| 6,053,909 A | 4/2000 | Shadduck | |
| 6,104,959 A | 8/2000 | Spertell | |
| 6,110,182 A * | 8/2000 | Mowlai-Ashtiani | 606/130 |
| 6,139,876 A | 10/2000 | Kolta | |
| 6,149,646 A | 11/2000 | West, Jr. et al. | |
| 6,161,544 A | 12/2000 | DeVore et al. | |
| 6,162,210 A | 12/2000 | Shadduck | |
| 6,293,938 B1 | 9/2001 | Muller | |
| 6,319,273 B1 | 11/2001 | Chen et al. | |
| 6,325,792 B1 | 12/2001 | Swinger et al. | |
| 6,334,074 B1 | 12/2001 | Spertell | |
| 6,342,053 B1 | 1/2002 | Berry | |
| 6,402,739 B1 | 6/2002 | Neev | |
| 6,413,255 B1 | 7/2002 | Stern | |
| 6,520,956 B1 | 2/2003 | Huang | |
| 6,617,963 B1 | 9/2003 | Watters et al. | |
| 6,749,604 B1 | 6/2004 | Eggers et al. | |
| 6,946,440 B1 | 9/2005 | DeWoolfson et al. | |
| 7,044,945 B2 | 5/2006 | Sand | |
| 7,130,835 B2 | 10/2006 | Cox et al. | |
| 7,141,049 B2 | 11/2006 | Stern et al. | |
| 7,192,429 B2 | 3/2007 | Trembly | |
| 7,270,658 B2 | 9/2007 | Woloszko et al. | |
| 7,402,562 B2 | 7/2008 | DeWoolfson | |
| 7,651,506 B2 * | 1/2010 | Bova et al. | 606/130 |
| 7,713,268 B2 | 5/2010 | Trembly | |
| 2001/0021844 A1 * | 9/2001 | Kurtz et al. | 606/5 |
| 2001/0039422 A1 * | 11/2001 | Carol et al. | 606/130 |
| 2002/0002369 A1 | 1/2002 | Hood | |
| 2002/0013579 A1 | 1/2002 | Silvestrini | |
| 2002/0049437 A1 | 4/2002 | Silvestrini | |
| 2002/0077699 A1 | 6/2002 | Olivieri et al. | |
| 2002/0091323 A1 * | 7/2002 | Dreher | 600/476 |
| 2002/0091401 A1 | 7/2002 | Hellenkamp | 606/166 |
| 2002/0099363 A1 | 7/2002 | Woodward et al. | |
| 2002/0143326 A1 * | 10/2002 | Foley et al. | 606/41 |
| 2002/0164379 A1 | 11/2002 | Nishihara et al. | |
| 2003/0018255 A1 | 1/2003 | Martin et al. | |
| 2003/0097130 A1 | 5/2003 | Muller et al. | |
| 2003/0167061 A1 * | 9/2003 | Schlegel et al. | 606/130 |
| 2003/0175259 A1 | 9/2003 | Karageozian | |
| 2003/0216728 A1 | 11/2003 | Stern et al. | |
| 2004/0001821 A1 | 1/2004 | Silver et al. | |
| 2004/0111086 A1 | 6/2004 | Trembly | |
| 2004/0143250 A1 | 7/2004 | Trembly | |
| 2004/0199158 A1 | 10/2004 | Hood et al. | |
| 2004/0243160 A1 | 12/2004 | Shiuey et al. | |
| 2005/0033202 A1 | 2/2005 | Chow et al. | |
| 2005/0070977 A1 | 3/2005 | Molina | |
| 2005/0131401 A1 * | 6/2005 | Malecki et al. | 606/27 |
| 2005/0197657 A1 | 9/2005 | Goth et al. | |
| 2005/0287217 A1 | 12/2005 | Levin et al. | |
| 2006/0135957 A1 | 6/2006 | Panescu | |
| 2006/0149343 A1 | 7/2006 | Altshuler et al. | |
| 2006/0189964 A1 | 8/2006 | Anderson et al. | |
| 2006/0206110 A1 | 9/2006 | Knowlton et al. | |
| 2006/0254851 A1 | 11/2006 | Karamuk | |
| 2006/0287662 A1 | 12/2006 | Berry et al. | |
| 2007/0048340 A1 | 3/2007 | Ferren et al. | |
| 2007/0055227 A1 | 3/2007 | Khalaj et al. | |
| 2007/0074722 A1 | 4/2007 | Giroux et al. | |
| 2007/0114946 A1 | 5/2007 | Goetze et al. | |
| 2007/0123845 A1 | 5/2007 | Lubatschowski | |
| 2007/0161976 A1 | 7/2007 | Trembly | |
| 2007/0179564 A1 | 8/2007 | Harold | |
| 2007/0203547 A1 | 8/2007 | Costello et al. | |
| 2007/0244470 A1 | 10/2007 | Barker et al. | |
| 2007/0244496 A1 | 10/2007 | Hellenkamp | |
| 2008/0015660 A1 | 1/2008 | Herekar | |
| 2008/0027328 A1 | 1/2008 | Klopotek et al. | |
| 2008/0300590 A1 * | 12/2008 | Horne et al. | 606/35 |
| 2009/0024117 A1 | 1/2009 | Muller | |
| 2009/0054879 A1 | 2/2009 | Berry | |
| 2009/0069798 A1 | 3/2009 | Muller et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0187173 A1 | 7/2009 | Muller | |
| 2009/0209954 A1 | 8/2009 | Muller et al. | |
| 2010/0094197 A1 | 4/2010 | Marshall et al. | |

FOREIGN PATENT DOCUMENTS

| | | |
|---|---|---|
| EP | 2 269 531 | 1/2011 |
| FR | 2 818 119 A1 | 6/2002 |
| WO | WO 99/17690 | 4/1999 |
| WO | WO 00/09027 | 2/2000 |
| WO | 0074648 A2 | 12/2000 |
| WO | WO 03/002008 | 1/2003 |
| WO | WO 2004/052223 | 6/2004 |
| WO | 2006/128038 A2 | 11/2006 |
| WO | 2006128038 A2 | 11/2006 |
| WO | WO 2007/022993 | 3/2007 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Written Opinion of The International Searching Authority, dated Feb. 24, 2009.

Muller et al., Br. J. Opthalmol 2001; 85:437-443 (April).

Naoumidi et al., J. Cataract Refract Surg. May 2006; 32(5):732-41.

Pallikaris et al., J. Cataract Refract Surg. Aug. 2005; 31(8):1520-29.

Acosta et al., Cornea. Aug. 2006;25(7):830-8.

International Search Report for PCT/US2010/029806 dated Jun. 1, 2010 (3 pages).

Written Opinion for PCT/US2010/029806 dated Jun. 1, 2010 (6 pages).

International Search Report for PCT/US2010/029791 dated Jun. 1, 2010 (3 pages).

Written Opinion for PCT/US2010/029791 dated Jun. 1, 2010 (6 pages).

Trembly et al.; Microwave Thermal Keratoplasty for Myopia: Keratoscopic Evaluation in Procine Eyes; Journal of Refractive Surgery; vol. 17; Nov./Dec. 2001; (8 pages).

Berjano et al.; "Radio-Frequency Heating of the Cornea: Theoretical Model and In Vitro Experiments"; IEEE Transactions on Biomedical Engineering; vol. 49; No. 3; Mar. 2002; pp. 196-205.

Berjano et. al.; "Ring Electrode for Radio-Frequency Heating of the Cornea: Modelling and In Vitro Experiments"; Medical & Biological Engineering & Computing 2003; vol. 41; pp. 630-639.

International Search Report mailed Aug. 14, 2009 for PCT/US2009/042204, (5 pages).

International Search Report mailed Nov. 20, 2009 for PCT/2009/059061 (3 pages).

International Search Report mailed Nov. 6, 2009 for PCT/US2009/057481 (2 pages).

Alain Chandonnet et al., "CO2 Laser Annular Thermokeratoplasty: A Preliminary Study", Lasers in Surgery and Medicine 12:264-273 (1992), Wiley-Lill, Inc., pp. 264-273.

Alió JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).

Alió JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).

Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).

Andreassen TT, Simonsen AH, Oxlund H, "Biomechanical Properties of Keratoconus and Normal Corneas," *Experimental Eye Research*, vol. 31, Oct. 1980, pp. 435-441 (7 pages).

Anschutz T, "Laser Correction of Hyperopia and Presbyopia," *International Ophthalmology Clinics*, vol. 34, No. 4, Fall 1994, pp. 107-137 (33 pages).

Bailey MD, Zadnik K, "Outcomes of LASIK for Myopia With FDA-Approved Lasers," *Cornea*, vol. 26, No. 3, Apr. 2007, pp. 246-254 (9 pages).

Borja D, Manns F, Lamar P, Rosen A, Fernandez V, Parel JM, "Preparation and Hydration Control of Corneal Tissue Strips for Experimental Use," *Cornea*, vol. 23, No. 1, Jan. 2004, pp. 61-66 (7 pages).

Bower KS, Weichel ED, Kim TJ, "Overview of Refractive Surgery," *Am Fam Physician*, vol. 64, No. 7, Oct. 2001, pp. 1183-1190 (8 pages).

Braun EH, Lee J, Steinert RF, "Monovision in LASIK," *Ophthalmology*, vol. 115, No. 7, Jul. 2008, pp. 1196-1202 (7 pages).

Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).

Bryant MR, McDonnell PJ, "Constitutive Laws for Biomechanical Modeling of Refractive Surgery," *Journal of Biomechanical Engineering*, vol. 118, Nov. 1996, pp. 473-481 (10 pages).

Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).

Charman WN, "The Eye in Focus: Accommodation and Presbyopia," *Clinical and Experimental Optometry*, vol. 91, May 2008, pp. 207-225 (19 pages).

Corbett et al, "Effect of Collagenase Inhibitors on Coreal Haze after PRK", Exp. Eye Res., vol. 72, Issue 3, pp. 253-259, dated Jan. 29, 2001 (7 pages).

Cox CA, Krueger RR, "Monovision with Laser Vision Correction," *Ophthalmology Clinics of North Amermica*, vol. 19, No. 1, Mar. 2006, pp. 71-75 (7 pages).

Doss JD, Albillar JI, "A Technique for the Selective Heating of Corneal Stroma," *Contact & Intraocular Lens Medical Journal*, vol. 6, No. 1, Jan.- Mar. 1980, pp. 13-17 (8 pages).

Elsheikh A, Anderson K, "Comparative Study of Corneal Strip Extensometry and Inflation Tests," *Journal of the Royal Society Interface*, vol. 2, May 2005, pp. 177-185 (10 pages).

Evans BJW, "Monovision: a Review," *Ophthalmic and Physiological Optics*, vol. 27, Jan. 2007, pp. 417-439 (23 pages).

Gasset AR, Kaufman HE, "Thermokeratoplasty in the Treatment of Keratoconus," *American Journal of Ophthalmology*, vol. 79, Feb. 1975, pp. 226-232 (8 pages).

Gloster J, Perkins ES, "The Validity of the Imbert-Flick Law as Applied to Applanation Tonometry," *Experimental Eye Research*, vol. 2, Jul. 1963, pp. 274-283 (10 pages).

Gupta N, Naroo SA, "Factors Influencing Patient Choice of Refractive Surgery or Contact Lenses and Choice of Centre," *Contact Lens & Anterior Eye*, vol. 29, Mar. 2006, pp. 17-23 (7 pages).

Hamilton DR, Hardten DR, Lindstrom RL, "Thermal Keratoplasty," *Cornea*, $2^{nd}$ Edition, Chapter 167, 2005, pp. 2033-2045 (13 pages).

Hersh PS, "Optics of Conductive Keratoplasty: Implication for Presbyopia Management," *Transactions of the American Ophthalmological Society*, vol. 103, 2005, pp. 412-456 (45 pages).

Hjortdal JO, "Extensibility of the Normo-Hydrated Human Cornea," *Acta Ophthalmologica Scandinavica*, vol. 73, No. 1, Feb. 1995, pp. 12-17 (7 pages).

Hori-Komai Y, Toda I, Asano-Kato N, Tsubota K, "Reasons for Not Performing Refractive Surgery," *Journal of Cataract & Refractive Surgery*, vol. 28, May 2002, pp. 795-797 (3 pages).

Illueca C, Alió JL, Mas D, Ortiz D, Pérez J, Espinosa J, Esperanza S, "Pseudoaccommodation and Visual Acuity with Technovision PresbyLASIK and a Theoretical Simulated Array® Multifocal Intraocular Lens," *Journal of Refractive Surgery*, vol. 24, Apr. 2008, pp. 344-349 (6 pages).

Jain S, Arora I, Azar DT, "Success of Monovision in Presbyopes: Review of the Literature and Potential Applications to Refractive Surgery," *Survey of Ophthalmology*, vol. 40, No. 6, May-Jun. 1996, pp. 491-499 (9 pages).

Jin GJC, Lyle A, Merkley KH, "Laser in Situ Keratomileusis for Primary Hyperopia," *Journal of Cataract & Refractive Surgery*, vol. 31, Apr. 2005, pp. 776-784 (9 pages).

Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).

Llovet F, Galal A, Benitez-del-Castillo J-M, Ortega J, Martin C, Baviera J, "One-Year Results of Excimer Laser in Situ Keratomileusis for Hyperopia," *Journal of Cataract & Refractive Surgery*, vol. 35, Jul. 2009, pp. 1156-1165 (10 pages).

Loarie TM, Applegate D, Kuenne CB, Choi LJ, Horowitz DP, "Use of Market Segmentation to Identify Untapped Consumer Needs in Vision Correction Surgery for Future Growth," *Journal of Refractive Surgery*, vol. 19, No. 5, Sep.-Oct. 2003, pp. 566-576 (12 pages).

Maxwell WA, Lane SS, Zhou F, "Performance of Presbyopia-Correcting Intraocular Lenses in Distance Optical Bench Tests," *Journal of Cataract & Refractive Surgery*, vol. 35, Jan. 2009, pp. 166-171 (6 pages).

McDonald MB, Durrie D, Asbell P, Maloney R, Nichamin L, "Treatment of Presbyopia With Conductive Keratoplasty: Six-Month Results of the 1-Year United States FDA Clinical Trial," *Cornea*, vol. 23, No. 7, Oct. 2004, pp. 661-668 (8 pages).

McDonald MB, "Conductive Keratoplasty: a Radiofrequency-Based Technique for the Correction of Hyperopia," *Transactions of the American Ophthalmological Society*, vol. 103, Dec. 2005, pp. 512-536 (25 pages).

Moriera MD, Garbus JJ, Fasano A, Lee M, Clapham TN, McDonnel PJ, "Multifocal Corneal Topographic Changes With Excimer Laser Photorefractive Keratectomy," *Archives of Ophthalmology*, vol. 110, Jul. 1992, pp. 994-999 (6 pages).

Nash IS, Greene PR, Foster CS, "Comparison of Mechanical Properties of Keratoconus and Normal Corneas," *Experimental Eye Research*, vol. 35, 1982, pp. 413-424 (12 pages).

Newman JM, "Analysis, Interpretation, and Prescription for the Ametropias and Heterophorias," *Borish's Clinical Refraction*, 1998, pp. 776-822 (49 pages).

Pandolfi A, Manganiello F, "A Model for the Human Cornea: Formulation and Numerical Analysis," *Biomechanics and Modeling in Mechanobiology*, vol. 5, Jan. 2006, pp. 237-246 (10 pages).

Pertaub R, Ryan TP, "Numerical Model and Analysis of an Energy-Based System Using Microwaves for Vision Correction," *Proceedings of SPIE*, vol. 7181, Feb. 2009, p. 718105-1 to 718105-14 (14 pages).

Petroll WM, Roy P, Chuong CJ, Hall B, Cavanagh HD, Jester JV, "Measurement of Surgically Induced Corneal Deformations Using Three-Dimensional Confocal Microscopy," *Cornea*, vol. 15, No. 2, Mar. 1996, pp. 154-164 (12 pages).

Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," *Journal of Refractive Surgery*, vol. 24, May 2008, pp. 494-500 (7 pages).

Pinsky PM, Datye DV, "A Microstructurally-Based Finite Element Model of the Incised Human Cornea," *Journal of Biomechanics*, vol. 24, No. 10, Apr. 1991, pp. 907-922 (15 pages).

Pinsky PM, Datye DV, "Numerical Modeling of Radial, Astigmatic, and Hexagonal Keratotomy," *Refractive and Corneal Surgery*, vol. 8, No. 2, Mar.-Apr. 1992, pp. 164-172 (11 pages).

Pinsky PM, van der Heide D, Chernyak D, "Computational Modeling of Mechanical Anisotropy in the Cornea and Sclera," *Journal of Cataract & Refractive Surgery*, vol. 31, Jan. 2005, pp. 136-145 (10 pages).

Riley C, Chalmers RL, "Survey of Contact Lens-Wearing Habits and Attitudes Toward Methods of Refractive Correction: 2002 Versus 2004," *Optometry and Vision Science*, vol. 82, No. 6, Jun. 2005, pp. 555-561 (7 pages).

Rosenbloom A, "New Aged and Old Aged: Impact of the Baby Boomer," *Journal of the American Optometry Association*, vol. 74, No. 4, Apr. 2003, pp. 211-213 (5 pages).

Rutzen AR, Roberts CW, Driller J, Gomez D, Lucas BC, Lizzi FL, Coleman DJ., "Production of Corneal Lesions Using High-Intensity Focused Ultrasound," *Cornea*, vol. 9, No. 4, Oct. 1990, pp. 324-330 (8 pages).

Ryan TP, Pertaub R, Meyers SR, Dresher RP, Scharf R., "Experimental Results of a New System Using Microwaves for Vision Correction," *Proceedings of SPIE*, vol. 7181, Feb. 2009, pp. 718106.1 to 718106.17 (17 pages).

Seiler T, Matallana M, Bende T, "Laser Thermokeratoplasty by Means of a Pulsed Holmium:YAG Laser for Hyperopic Correction," *Refractive and Corneal Surgery*, vol. 6, No. 5, Sep.-Oct. 1990, pp. 335-339 (6 pages).

Seiler T, Matallana M, Sendler S, Bende T, "Does Bowman's Layer Determine the Biomechanical Properties of the Cornea?" *Refractive and Corneal Surgery*, vol. 8, No. 2, Mar.-Apr. 1992, pp. 139-142 (6 pages).

Shin TJ, Vito RP, Johnson LW, McCarey BE, "The Distribution of Strain in the Human Cornea," *Journal of Biomechanics*, vol. 30, No. 5, May 1997, pp. 497-503 (7 pages).

Solomon KD, Fernandez de Castro LE, Sandoval HP, Biber JM, Groat B, Neff KD, Ying MS, French JW, Donnenfeld ED, Lindstrom RL, "LASIK World Literature Review: Quality of Life and Patient Satisfaction," *Ophthalmology*, vol. 116, No. 4, Apr. 2009, pp. 691-701 (11 pages).

Stanley PF, Tanzer DJ, Schallhorn SC, "Laser Refractive Surgery in the United States Navy," *Current Opinion Ophthalmology*, vol. 19, Jul. 2008, pp. 321-324 (4 pages).

Strenk SA, Strenk LM, Koretz JF, "The Mechanism of Presbyopia," *Progress in Retinal Eye Research*, vol. 24, May 2005, pp. 379-393 (15 pages).

Stringer H, Parr J., "Shrinkage Temperature of Eye Collagen," *Nature*, Dec. 1964, p. 1307 (1 page).

Sutton G., Patmore A.L., Joussen A.M., Marshall J., "Mannose 6-Phosphate Reduces Haze Following Excimer Laser Photorefractive Keratectomry," *Lasers and Light*, vol. 7, No. 2/3, 1996, pp. 117-119 (3 pages).

Telandro A., "Pseudo-Accommodation Cornea: a New Concept for Correction of Presbyopia," *Journal of Refractive Surgery*, vol. 20, No. 5, Sep.-Oct. 2004, pp. S714-S717 (5 pages).

Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).

Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).

Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).

Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-1111 (7 pages).

Wang JQ, Zeng YJ, Li XY, "Influence of Some Operational Variables on the Radial Keratotomy Operation," *British Journal of Ophthalmology*, vol. 84, Jan. 2000, pp. 651-6533 (4 pages).

Wollensak, G., et al., "Riboflavin/Ultraviolet-A-Induced Collagen Crosslinking for the Treatment of Keratoconus," *American Journal of Ophthalmology*, Ophthalmic Publ., Chicago, IL, US, vol. 135, No. 5, May 1, 2003, pp. 620-627 (8 pages).

Zelichowska B, Rę kas M, Stankiewicz A, Cervino A, Montés-Micó R., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).

Extended Search Report for European Application No. 09704081.0 dated Nov. 30, 2012 (5 pages).

\* cited by examiner

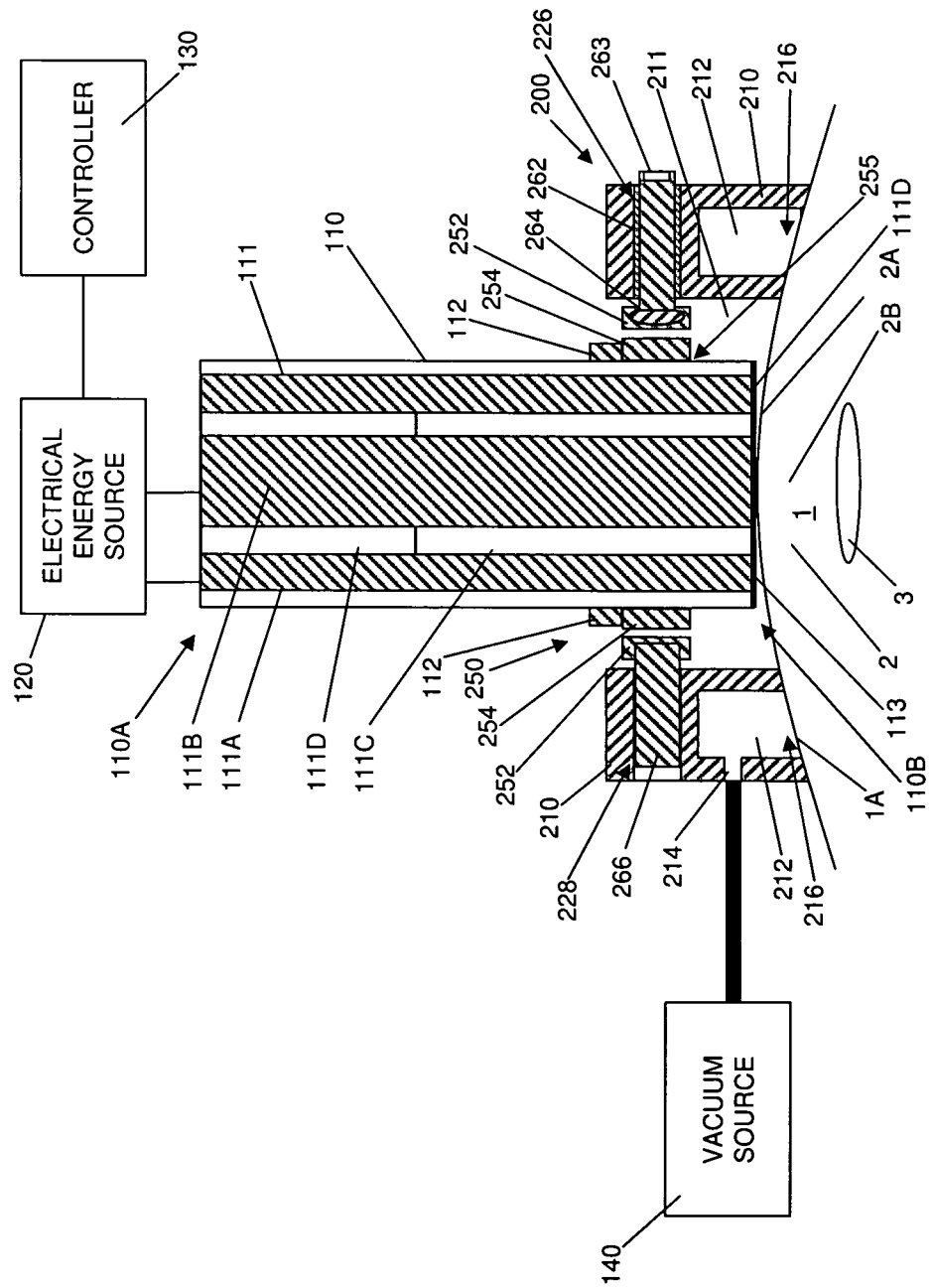

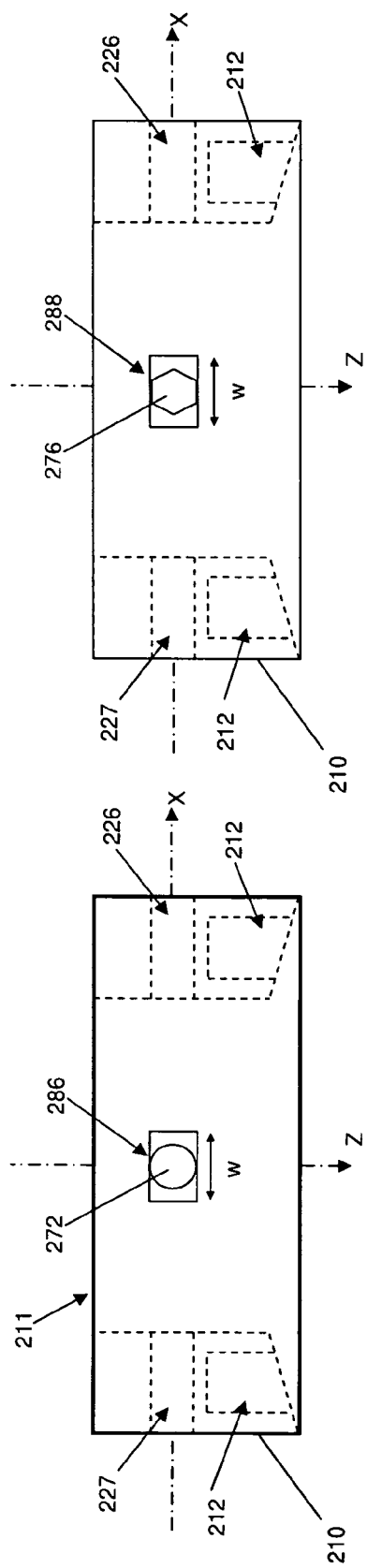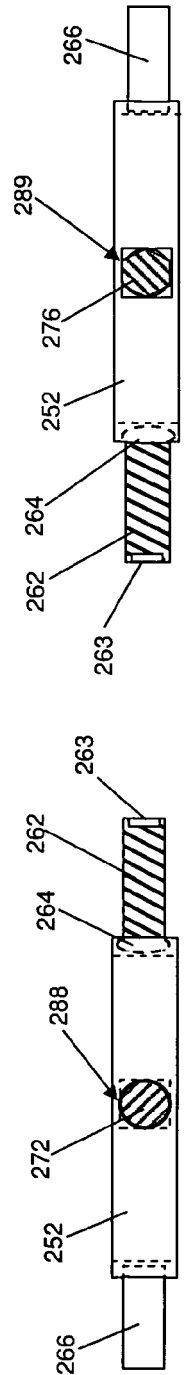

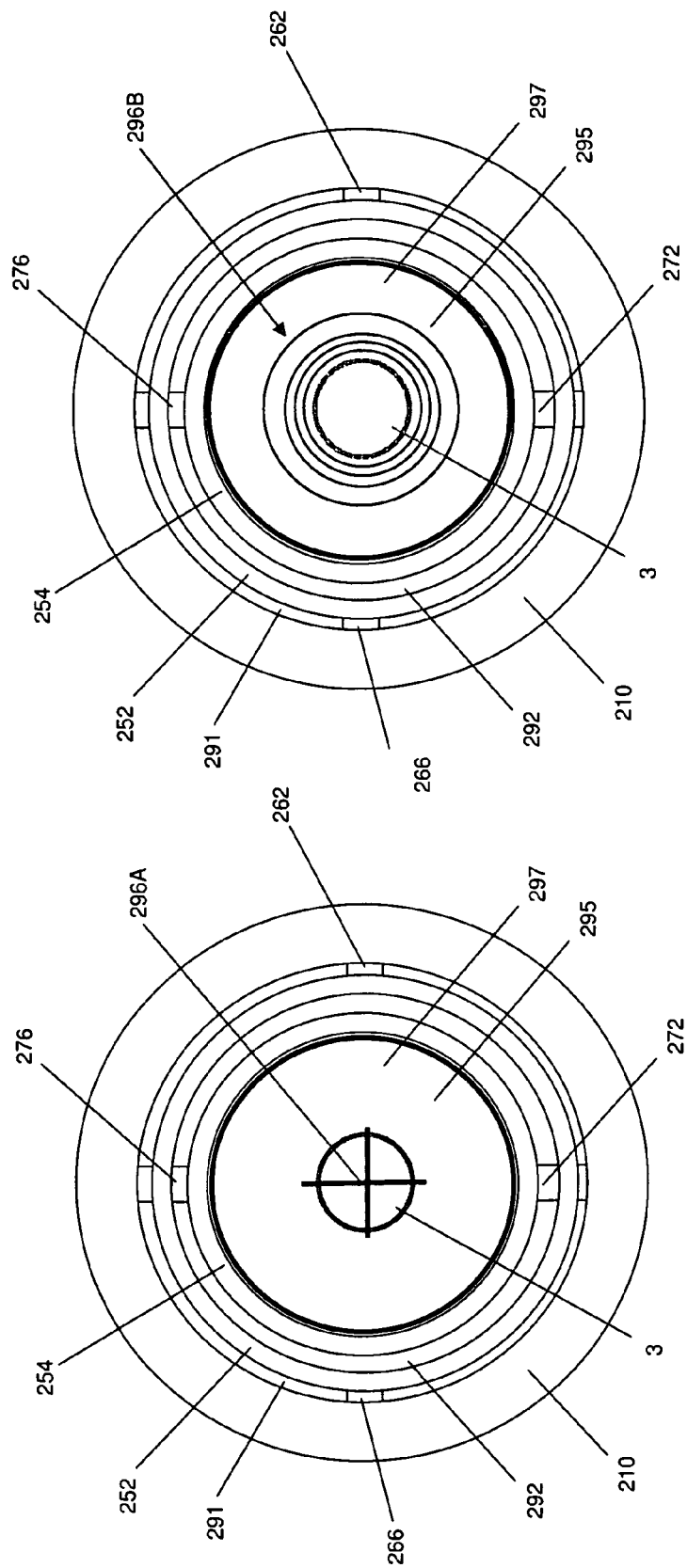

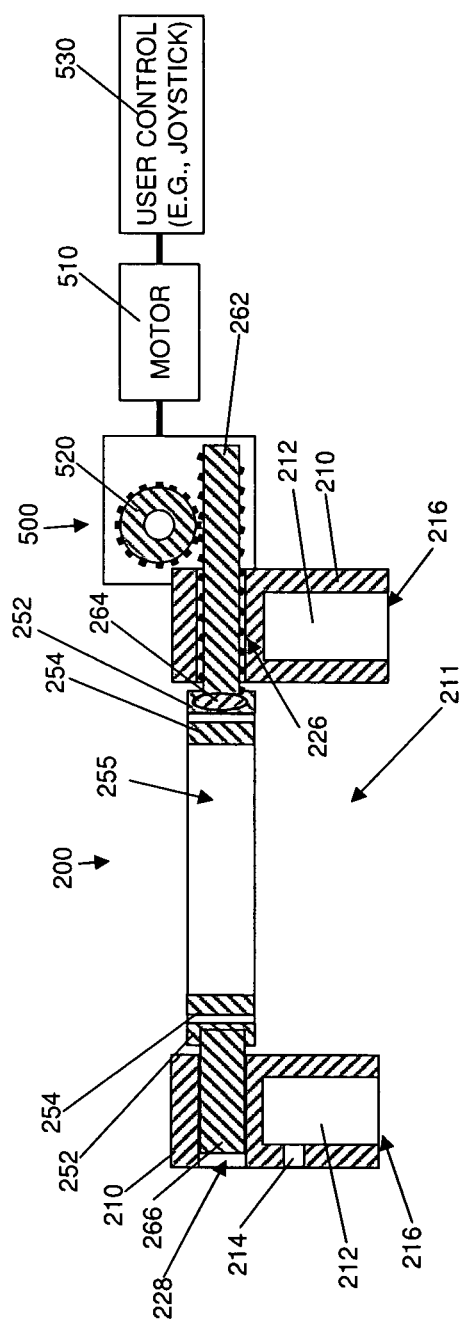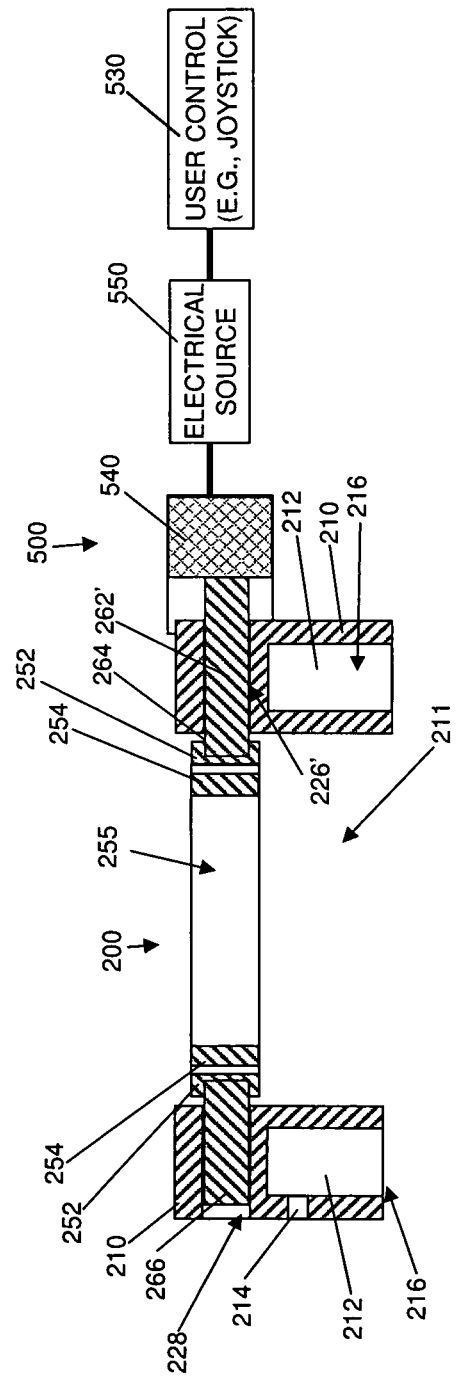
FIG. 12A
FIG. 12B

SYSTEM AND METHOD FOR POSITIONING AN EYE THERAPY DEVICE

BACKGROUND OF THE INVENTION

1. Field of the Invention

The invention pertains generally to the field of keratoplasty and, more particularly, to a system and method for accurately positioning an applicator for thermokeratoplasty to deliver energy to targeted areas of corneal fibrils in an eye.

2. Description of Related Art

A variety of eye disorders, such as myopia, keratoconus, and hyperopia, involve abnormal shaping of the cornea. Keratoplasty reshapes the cornea to correct such disorders. For example, with myopia, the shape of the cornea causes the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratonomileusis (LASIK), may be employed to reshape the cornea. However, such surgical procedures typically require a healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty, for example, may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of energy in circular, ring-shaped patterns around the pupil generates heat that may cause aspects of the cornea to flatten. Improved vision results from this process if the energy is accurately applied to targeted areas of the cornea and the cornea achieves the desired shape. Therefore, an important aspect of thermokeratoplasty is the manner in which the device applying energy to the cornea is positioned to deliver the energy.

SUMMARY OF THE INVENTION

In view of the foregoing, embodiments according to aspects of the present invention provide a system and method for accurately positioning an applicator to deliver eye therapy to targeted areas of the eye. In particular, embodiments provide a system and method for accurately positioning an applicator for thermokeratoplasty to deliver energy to targeted areas of corneal fibrils in an eye. Advantageously, embodiments provide an improved system and method for achieving a desired reshaping of a cornea to improve vision through the eye.

Accordingly, an embodiment of the present invention provides an attachment element that is removably attached to a surface of an eye. A receiving element is coupled to the attachment element and movable relative to the attachment element. The receiving element includes a coupling element configured to operably couple an eye therapy instrument to the receiving element and adjustably move the eye therapy instrument into a selected position with respect to the attachment element.

A system for aligning an eye therapy instrument over a selected area of an eye provides an attachment element that is removably attached to a surface of an eye. A receiving element is coupled to the attachment element and movable relative to the attachment element. The receiving element includes a coupling element configured to operably couple an eye therapy instrument to the receiving element and adjustably move the eye therapy instrument into a selected position with respect to the attachment element. The system makes adjustments to ensure accurate delivery of treatment from the eye therapy device to areas of the eye. In one embodiment, the receiving element allows lateral adjustments to be made along one or more axes. Additionally or alternatively, the receiving element allows angular or rotational adjustments to be made about one or more axes.

In another embodiment, a system for aligning an eye therapy instrument over a feature of an eye provides an engagement element engaging an eye therapy instrument. A first positioning element is operably coupled to the engagement element and is configured to position the eye therapy instrument in a first location over a surface of an eye. Meanwhile, a second positioning element is operably coupled to the engagement element and configured to adjustably position the eye therapy instrument from the first position to a second position over the surface of the eye.

In yet another embodiment, a method for aligning an eye therapy instrument over a feature of an eye includes the steps of attaching an attachment element to a surface of an eye, positioning a receiving element over a feature of the eye, the receiving element being operably coupled to the attachment element and movable relative to the attachment element, and coupling an eye therapy instrument to the receiving element.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 1 illustrates an embodiment employing a positioning system that accurately positions an applicator to deliver energy to targeted areas of corneal fibrils in an eye.

FIG. 4A illustrates one side of the attachment element of the embodiment of FIG. 1

FIG. 4B illustrates another side of the attachment element of the embodiment of FIG. 1

FIG. 5A illustrates one side of the first ring of the embodiment of FIG. 1.

FIG. 5B illustrates another side of the first ring of the embodiment of FIG. 1.

FIG. 6A illustrates one side of the second ring of the embodiment of FIG. 1.

FIG. 6B illustrates another side of the second ring of the embodiment of FIG. 1.

FIG. 7A illustrates a targeting device for the embodiment of FIG. 1.

FIG. 7B illustrates another targeting device for the embodiment of FIG. 1.

FIG. 12A illustrates an embodiment employing an adjustment system for automated positioning of an applicator to deliver energy to targeted areas of corneal fibrils in an eye.

FIG. 12B illustrates another embodiment employing an adjustment system for automated positioning of an applicator to deliver energy to targeted areas of corneal fibrils in an eye.

DETAILED DESCRIPTION

Figure 2A:
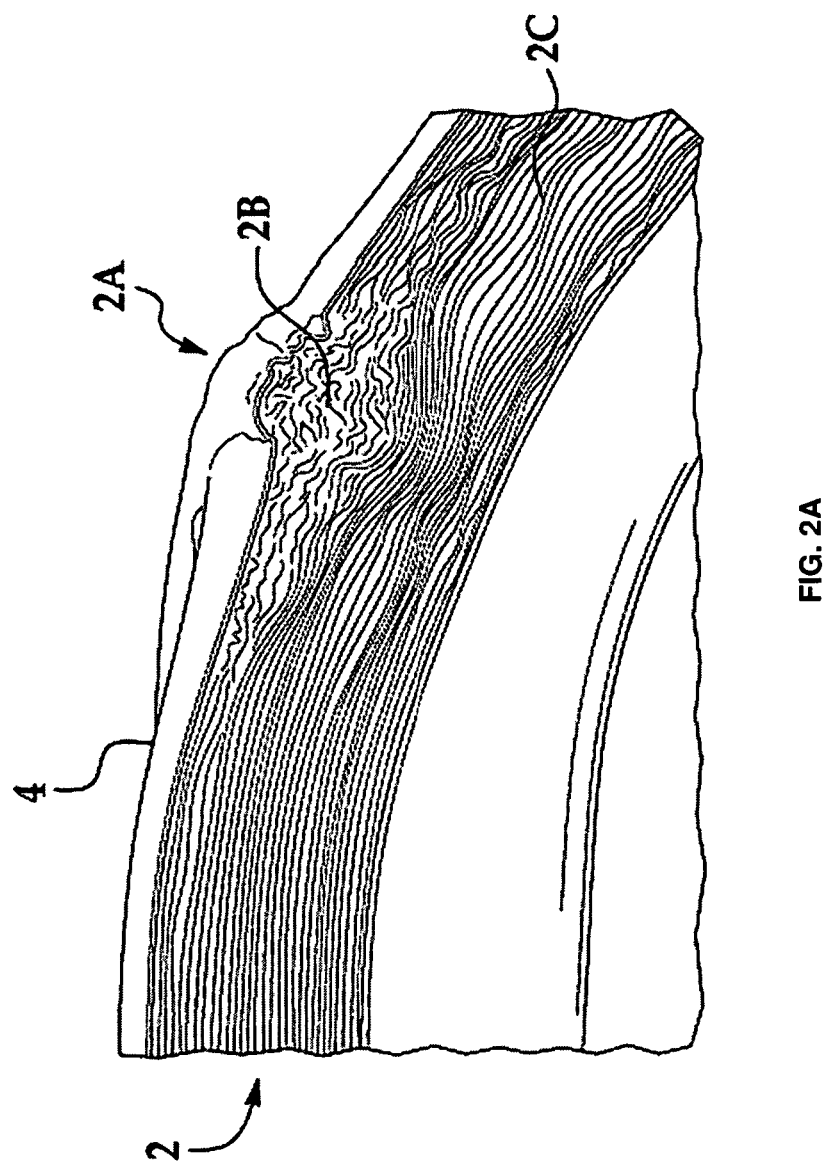
FIG. 2A illustrate a high resolution image of a cornea after energy has been applied.

Referring to the cross-sectional view of FIG. 1, a system for applying energy to a cornea 2 of an eye 1 to achieve corrective reshaping of the cornea is illustrated. In particular, FIG. 1 shows an applicator 110 that houses an energy conducting element 111. The energy conducting element 111 extends through the applicator 110 from a proximal end 110A to a distal end 110B. An electrical energy source 120 is operably connected to the energy conducting element 111 at the distal end 110B, for example, via conventional conducting cables. The electrical energy source 120 may include a microwave oscillator for generating microwave energy. For example, the oscillator may operate at a microwave frequency range of 500 MHz to 3000 MHz, and more specifically at a frequency of around 915 MHz which provides safe use of the energy conducting element 111. Although embodiments described herein may employ microwave frequencies, it is contemplated that any frequency, e.g., including microwave, radio-frequency (RF), etc., may be employed. For example, embodiments may employ radiation having, but not limited to, a frequency between 10 MHz and 300 GHz.

Operation of the energy source 120 causes energy to be conducted through the energy conducting element 111 to the distal end 110B. As such, the applicator 10 may be employed to apply energy to the cornea 2 of the eye 1 which is positioned at or near the distal end 110B. As shown further in FIG. 1, the distal end 110B is positioned over the cornea 2 by an adjustable positioning system 200. In general, the positioning system 200 provides support for the applicator 110 so that the applicator 110 can be operated to deliver energy to targeted areas of the cornea 2. The positioning system 200 includes an attachment element 210 and a receiving element 250. The applicator 110 is received into the receiving element 250, which in turn is coupled to the attachment element 210. Meanwhile, the attachment element 210 is fixed to a portion of the eye surface 1A, such as the area surrounding the cornea. The receiving element 250 can move relative to the attachment element 210 when the attachment element 210 is fixed in place. As such, the receiving element 250 can be adjusted so that the applicator 110 is positioned over the targeted areas of the cornea 2. When adjustments using the receiving element 250 are completed, the position of the receiving element 250 with respect to the attachment element 210 remains fixed or set relative to the attachment element 210. In some embodiments, a locking mechanism may be employed. Accordingly, with the attachment element 210 attached to the eye surface 1A, the receiving element 250 fixed with respect to the attachment element 210, and the applicator 110 received into the receiving element 250, the applicator 110 is situated in a stable position for delivering energy to the cornea 2.

In general, the receiving element 250 may be centered relative to a center of the pupil, an apex of the cornea, or the like. When applying energy to the cornea 2 with an energy conducting element 111 as shown in FIG. 1, it may be desirable to center the energy conducting element 111 over the pupil 3 rather than other features of the eye 1. The pupil 3 is generally coincident with the center of the cornea 2. As such, centering the energy conducting element 111 over the pupil 3 causes the cornea to be reshaped with respect to the pupil 3, resulting in a more effective improvement in vision. In addition, proper positioning of the energy conducting element 111 minimizes the likelihood of unintended delivery of energy and heat-related damage to certain areas of the eye 1. It has been discovered that because the cornea is domelike or even conical in shape, conventional devices for positioning therapy devices in relation to an eye 1 tend to become centered with respect to the domelike or conical aspect of the cornea 2 rather than the actual center of the cornea 2, or the pupil 3, within the eye 1. Accordingly, the embodiments described herein address a heretofore unanticipated and unforeseen need for a positioning device that centers an eye therapy device, such as the energy conducting element 111, over a specific area, such as the pupil 3, of the eye 1. Advantageously, embodiments according to aspects of the present invention allow the receiving element 250 to move relative to the attachment element 210 and enable adjustments to be made after the attachment element 210 is fixed on the eye surface 1A. As a result, when the receiving element 250 receives the applicator 110, the energy conducting element 111 is properly positioned with respect to the eye 1.

Once the applicator 110 is positioned by the positioning system 200, the energy conducting element 111 can deliver energy to targeted areas of collagen fibers in a mid-depth region 2B of the cornea 2 to shrink the collagen fibers according to a predetermined pattern and reshape the cornea 2 in a desired manner, thereby improving vision through the eye 1. For example, a contribution to the corneal reshaping comes from the contraction of the collagen fibrils found in the upper third of the corneal stroma, lying approximately 75-150 microns below the corneal, i.e., epithelial, surface 2A. Although not shown in FIG. 1, it is contemplated that embodiments may employ a coolant system that selectively applies coolant to the corneal surface to minimize heat-related damage to the corneal surface 2A during thermokeratoplasty and to determine the depth of energy delivered below the corneal surface 2A to the mid-depth region 2B. The coolant may be a liquid cryogen, such as tetrafluorothane. Alternatively, the coolant may be a cool gas, such as nitrogen gas, e.g., blowoff from a liquid nitrogen source. In some embodiments, the coolant may also be applied after the application of energy to preserve, or "set," the desired shape changes by eliminating further presence of energy and preventing further changes to the new corneal shape. Examples of such a coolant system are described in U.S. application Ser. No. 11/898,189, filed Sep. 10, 2007, the contents of which are entirely incorporated herein by reference.

As further illustrated in FIG. 1, the electrical energy conducting element 111 may include two microwave conductors 111A and 111B, which extend from the proximal end 110A to the distal end 110B of the applicator 110. For example, the conductor 111A may be a substantially cylindrical outer conductor, while the conductor 111B may be a substantially cylindrical inner conductor that extends through an inner passage extending through the outer conductor 111A. With the inner passage, the outer conductor 111A has a substantially tubular shape. The inner and the outer conductors 111A and 111B may be formed, for example, of aluminum, stainless steel, brass, copper, other metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D, or other material, may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 110A, the electrical energy generated by the electrical energy source 120, and directs microwave energy to the distal end 111B, where the cornea 2 is positioned by the positioning system 200.

The outer diameter of the inner conductor 111B is preferably larger than the pupil 3, over which the applicator 110 is centered. In general, the outer diameter of the inner conductor 111B may be selected to achieve an appropriate change in corneal shape, i.e. keratometry, induced by the exposure to microwave energy. The outer diameter of the inner electrode 111B determines the diameter across which the refractive change to the cornea 2 is made. When the energy conducting element is applied to the corneal surface 2A, the area of the cornea 2 at the periphery of the inner electrode 111B is subject to an energy pattern with substantially the same shape and dimension as the gap 111C between the two microwave conductors 111A and 111B.

Meanwhile, the inner diameter of the outer conductor 111A may be selected to achieve a desired gap between the conductors 111A and 111B. For example, the outer diameter of the inner conductor 111B ranges from about 4 mm to about 10 mm while the inner diameter of the outer conductor 111A ranges from about 4.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of energy by the applicator 110.

A controller 130 may be employed to selectively apply the energy any number of times according to any predetermined or calculated sequence. In addition, the energy may be applied for any length of time. Furthermore, the magnitude of energy being applied may also be varied. Adjusting such parameters for the application of energy determines the extent of changes that are brought about within the cornea 2. Of course, the system attempts to limit the changes in the cornea 2 to an appropriate amount of shrinkage of collagen fibrils in a selected region. When delivering microwave energy to the cornea 2 with the applicator 110, the microwave energy may be applied with low power (of the order of 40 W) and in long pulse lengths (of the order of one second). However, other systems may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may optionally be coated with a material that can function both as an electrical insulator as well as a thermal conductor. A dielectric layer 111D may be employed along the distal end 111B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 111D is positioned between the conductors 111A and 111B and the cornea 2. The dielectric layer 111D may be sufficiently thin to minimize interference with microwave emissions and thick enough to prevent superficial deposition of electrical energy by flow of conduction current. For example, the dielectric layer 111D may be a biocompatible material, such as Teflon®, deposited to a thickness of about 0.002 inches. In general, an interposing layer, such as the dielectric layer 111D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired energy pattern in the cornea 2. Of course, the dielectric material 111D may be omitted and electrical energy in the microwave or radio frequency (RF) band may be applied directly.

During operation, the distal end 110B of the applicator 110 as shown in FIG. 1 is positioned by the positioning system 200 on or near the corneal surface 2A. Preferably, the applicator 110 makes direct contact, or near contact, with the corneal surface 2A. As such, the conductors 111A and 111B are positioned at the corneal surface 2A (or substantially near the corneal surface 2A if there is a thin interposing layer between the conductors 111A and 111B and the corneal surface 2A). Accordingly, direct contact helps ensure that the pattern of microwave energy delivered to the corneal tissue has substantially the same shape and dimension as the gap 111C between the two microwave conductors 111A and 111B.

Figure 2B:
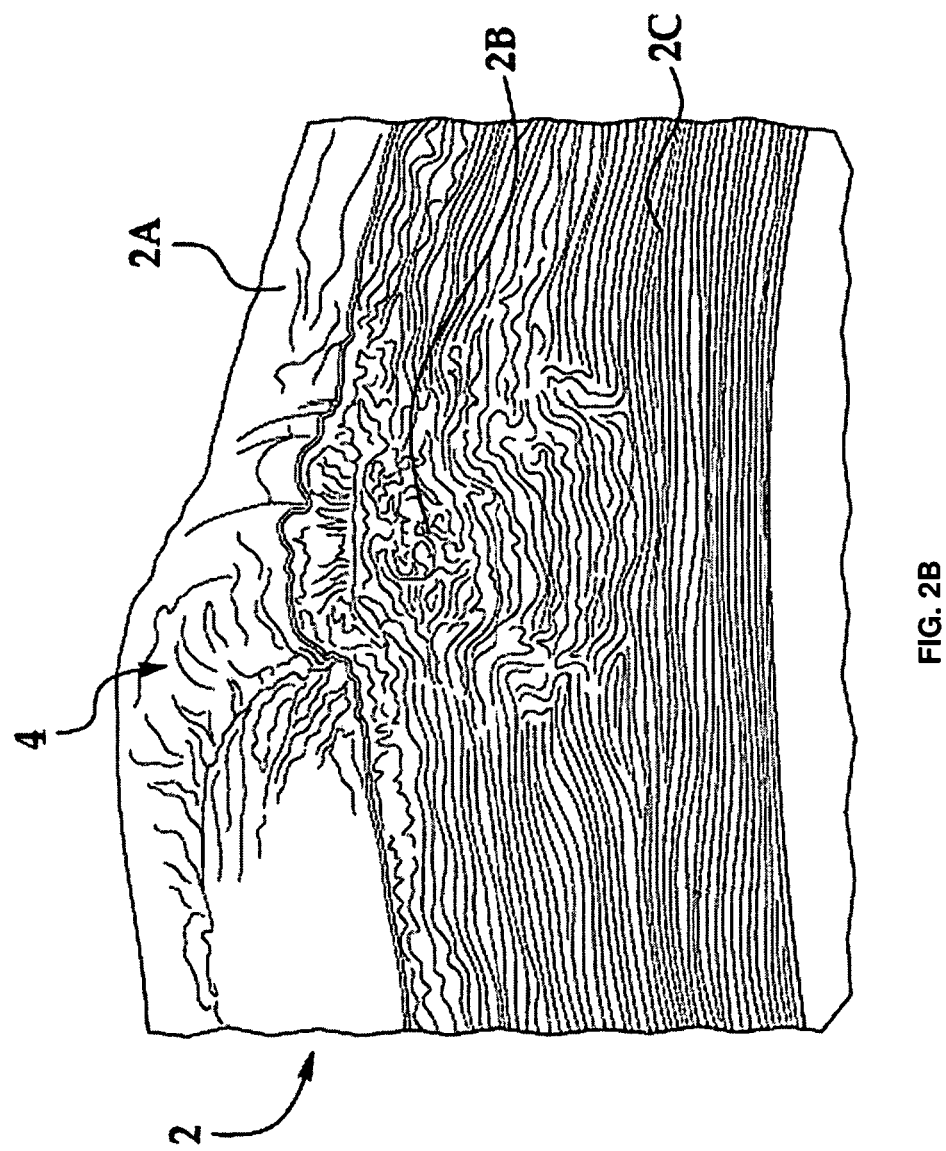
FIG. 2B illustrates another high resolution images of the cornea of FIG. 2A.

FIGS. 2A-D illustrate an example of the effect of applying energy to corneal tissue with a system for applying energy, such as the system illustrated in FIG. 1. In particular, FIGS. 2A and 2B illustrate high resolution images of cornea 2 after energy has been applied. As FIGS. 2A and 2B show, a lesion 4 extends from the corneal surface 2A to a mid-depth region 2B in the corneal stroma 2C. The lesion 4 is the result of changes in corneal structure induced by the application of energy as described above. These changes in structure result in an overall reshaping of the cornea 2. It is noted that the application of energy, however, has not resulted in any heat-related damage to the corneal tissue.

Figure 2C:
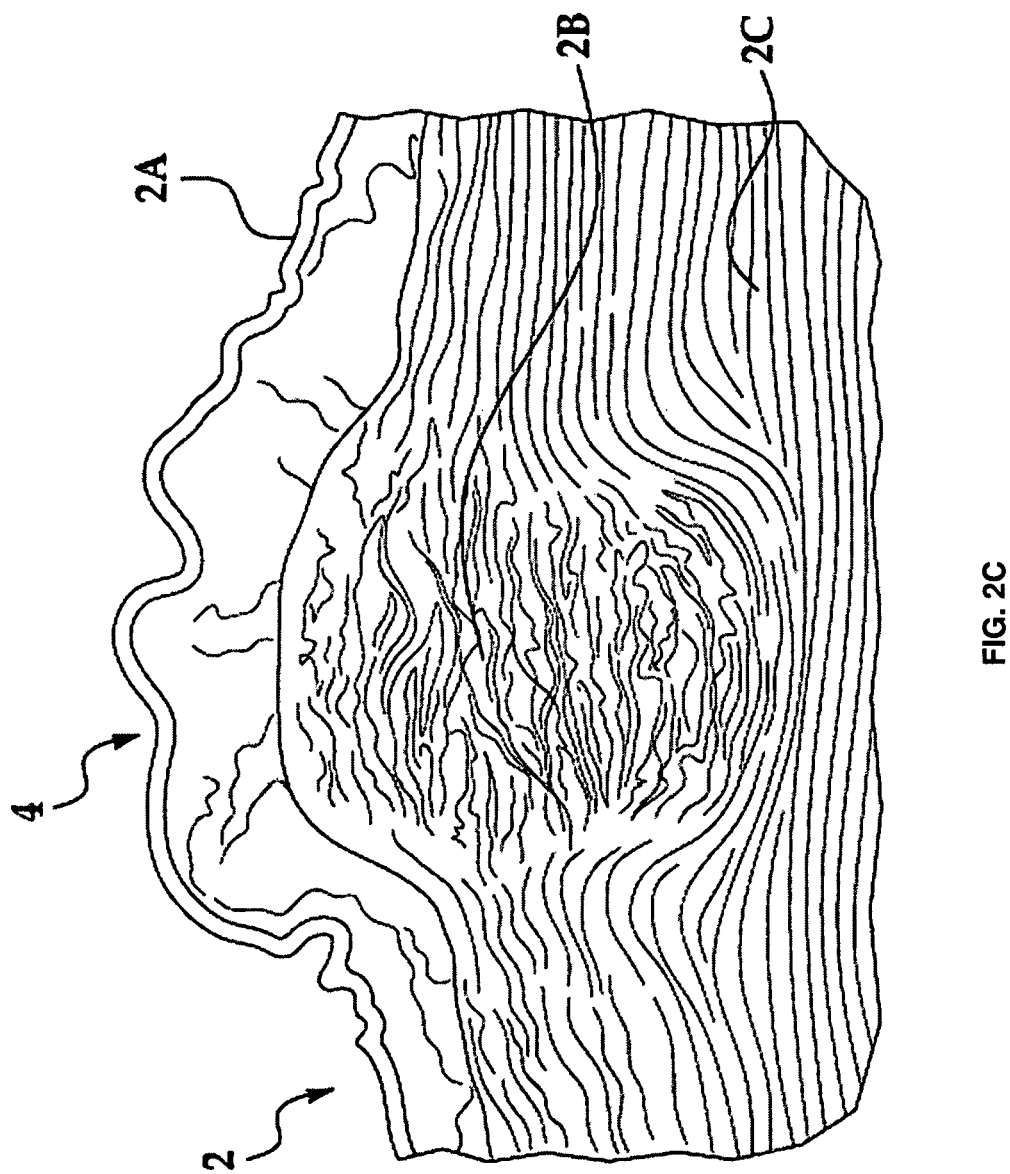
FIG. 2C illustrates a histology image of the cornea of FIG. 2A.
Figure 2D:
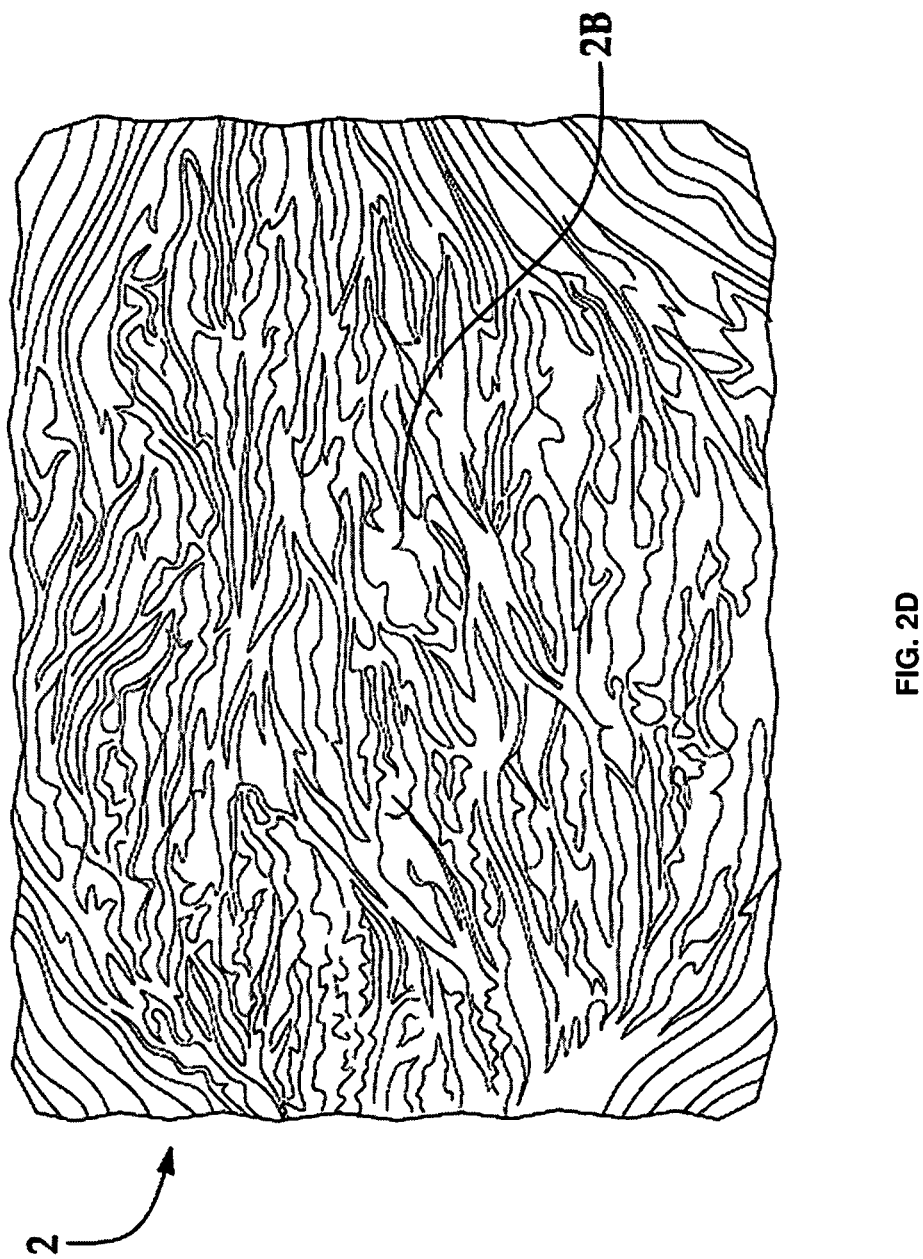
FIG. 2D illustrates another histology image of the cornea of FIG. 2A.

As further illustrated in FIGS. 2A and 2B, the changes in corneal structure are localized and limited to an area and a depth specifically determined by an applicator as described above. FIGS. 2C and 2D illustrate histology images in which the tissue shown in FIGS. 2A and 2B has been stained to highlight the structural changes induced by the energy. In particular, the difference between the structure of collagen fibrils in the mid-depth region 2B where energy has penetrated and the structure of collagen fibrils outside the region 2B is clearly visible. Thus, the collagen fibrils outside the region 2B remain generally unaffected by the application of energy, while the collagen fibrils inside the region 2B have been rearranged and formed new bonds to create completely different structures.

Accordingly, the final shape of the cornea 2 depends on which areas of collagen fibers receive the energy from the energy conducting element 111 and undergo shrinking. As described above, a positioning system 200 is employed to align the applicator 110 and deliver energy to targeted areas of the eye 1.

Figure 3:
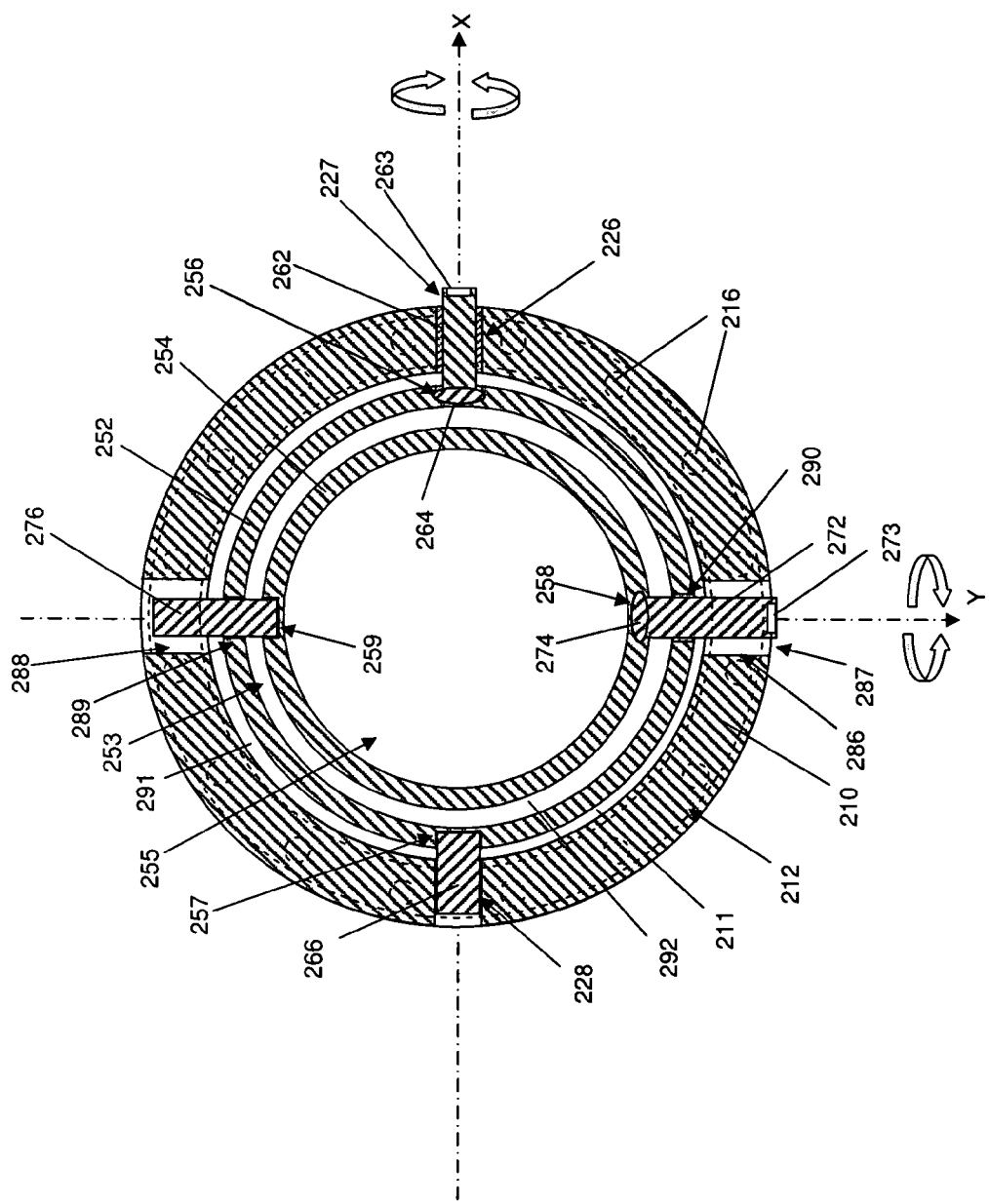
FIG. 3 illustrates a cross-sectional view of aspects of the embodiment of FIG. 1.

As shown in FIG. 1, the attachment element 210 of the positioning system 200 may have a substantially annular structure defining a central passageway 211. In some embodiments, for example, an outer diameter of the annular structure may range from approximately 18 mm to 23 mm while an inner diameter may range from approximately 11 mm to 15 mm to accommodate aspects of the eye 1 and the cornea 2. The attachment element 210 is attached to portions of the eye surface 1A by creating a vacuum connection with the eye surface 1A. The attachment element 210 of FIG. 1 includes an interior channel 212 which is operably connected to a vacuum source 140 via connection port 214. The attachment element 210 also includes a plurality of openings 216 which open the interior channel 212 to the eye surface 1A. FIG. 3 illustrates another view of the attachment element 210, including the central passageway 211, the interior channel 212, and the plurality of openings 216.

Therefore, when the openings 216 are positioned in contact with the eye surface 1A and the vacuum source 140 is activated to create a near vacuum or low pressure within the interior channel 212, the openings 216 operate to suction the attachment element 210 and the eye surface 1A together. To promote sufficient suction between the eye surface 1A and the attachment element 210, the bottom surface 213 of the attachment element 210 may be contoured to fit the shape of the eye more closely. In one example, the vacuum source 140 may be a syringe, but the vacuum source 140 may be any system that creates the appropriate amount of suction between the attachment element 210 and the eye surface 1A. Although the attachment element 210 can be stably attached to the eye surface 1A, the attachment element 210 can be detached by removing the vacuum source 140 and equalizing the pressure in the interior channel 212 with the exterior environment.

As further illustrated in FIG. 1, the receiving element 250 is operably coupled to the attachment element 210. The receiving element 250 of FIG. 1 includes a first ring, or substantially annular structure, 252 and a second ring, or substantially annular structure, 254. As described further below, the second ring 254 acts as a coupling element to couple the applicator 110 to the receiving element 250. The rings 252 and 254 are situated within the central passageway 211 of the attachment element 210, and the second ring 254 is situated in a ring passageway 253 of the first ring 252. A gap 291 separates the attachment element 210 and the first ring 252, while a gap 292 separates the first ring 252 and the second ring 254. FIG. 3 further illustrates the relationship between the attachment element 210 and the rings 252 and 254.

As shown in FIG. 3, a screw, or threaded element, 262 and a pin 266 couple the first ring 252 to the attachment element 210. In particular, the screw 262 extends through a threaded passageway 226 in the attachment element 210 and across the gap 291 to be received in a screw-end cavity 256 in the first ring 252. The screw-end cavity 256 is aligned with the threaded passageway 226 as shown in FIGS. 1 and 4. Meanwhile, directly opposite to the threaded element 262, the pin 266 extends from a pin passageway 228 in the attachment element 210 and across the gap 292 to be received into a pin-end cavity 257 in the first ring 252. The pin passageway 228 and the pin-end cavity 257 are aligned. Accordingly, the screw 262 supports one side of the first ring 252 within the central passageway 211 while the pin 266 supports the opposing side of the first ring 252.

The screw 262 and the pin 266 are aligned along an X-axis that extends across the attachment element 210, as shown in FIG. 3. Operation of the receiving element 250 enables the first ring to move laterally within the central passageway 211 along the X-axis. In particular, a head 263 of the screw 262 can be accessed with an appropriately sized screwdriver, or similar tool, at the opening 227 of the threaded passageway 226. When the tool engages the head 263, the screw 262 may be rotated about the X-axis. Such action causes the threads of the screw 262 to act against the threads of the threaded passageway 226 and to move the screw 262 along the X-axis. When turned in one direction, e.g. clockwise, the screw 262 moves further into the central passageway 211. When turned in the other direction, e.g. counterclockwise, the screw 262 moves outwardly away from the central passageway 211. Because the first ring 252 is attached to the screw 262 at the screw-end cavity 256, the first ring 252 moves with the screw 262 along the X-axis. The screw 262 engages the first ring 252 at the screw-end cavity 256 in a manner that allows the screw 262 to rotate freely within the screw-end cavity 256 while also allowing the screw 262 to cause lateral movement of the ring 252. For example, as shown in FIG. 4, the screw 262 may have an enlarged end 264 which is received, e.g. snapped, into interlocking engagement with the screw-end cavity 256. It is contemplated that other embodiments may use other techniques, such as a rivet-like attachment or the like, for coupling the screw 262 to the first ring 252, while still permitting rotation of the screw 262.

When the screw 262 moves within the threaded passageway 226, the pin 266 moves correspondingly within the pin passageway 228 of the attachment element 210. The pin passageway 228 provides minimal resistance as the pin 266 moves, e.g., slides, within the pin passageway 228. In some embodiments, bearings or similar guiding elements may be employed to facilitate movement of the pin 266 through the pin passageway 228. The pin 266 is in fixed abutment with the pin-end cavity 257 of the first ring 252, so that the pin 266 moves with the first ring 252 as the screw 262 moves the first ring 252 along X-axis. Accordingly, the pin 266 supports the first ring 252 while accommodating movement of the first ring 252 along the X-axis. Techniques for fixing the pin 266 to the first ring 252 may include, for example, welding, adhesive attachment, threaded engagement, interlocking engagement, tight frictional engagement, and the like. The pin 266 does not have to be equal in length to the pin passageway 228. In some embodiments, the length of the pin 266 may cause the pin 266 in some positions to extend outwardly from the pin passageway 228. Unlike the screw 262, the pin 266 is not threaded and does not rotate as it moves. Indeed, the pin 266 may have a non-cylindrical profile, e.g., rectangular, hexagonal, etc., that provides resistance to any rotation that the screw 262 may impart to the ring 252 when the screw 262 is rotated about X-axis. Such a profile is described further below.

As shown further in FIG. 3, a screw 272 and a pin 276 couple the second ring 254 to both the attachment element 210 and the first ring 252. In particular, the screw 272 extends through the screw passageway 286 in the attachment element 210, across the gap 291, through the threaded passageway 288 in the first ring 252, and across the gap 292 to be received into the screw-end cavity 258. The screw passageway 286, the threaded passageway 288, and the screw-end cavity 258 are aligned as shown in FIG. 3. Meanwhile, directly opposite the screw 272, the pin 276 extends from a pin passageway 287 in the attachment element 210, across the gap 291, through a pin passageway 289 of the first ring 252, and across the gap 292 to be received into a pin-end cavity 259 of the second ring 254. The pin passageway 287, the pin passageway 289, and the pin-end cavity 259 are aligned. Accordingly, the screw 272 supports one side of the second ring 254 within the ring passageway 253 of the first ring 252 while the pin 266 supports the opposing side of the second ring 254.

As shown in FIG. 3, the screw 272 and the pin 276 are aligned with a Y-axis that extends across the attachment element 210. Operation of the receiving element 250 enables the second ring 254 to move laterally within the central passageway 211 along the Y-axis. As illustrated in FIG. 3, the Y-axis and the X-axis are generally perpendicular to each other. Advantageously, the configuration shown in FIG. 3 ensures that the screw 262 and the pin 266 do not lock up movement along the Y-axis and that the screw 272 and the pin 276 do not lock up movement along the X-axis.

FIGS. 4A-B, 5A-B, and 6A-B illustrate in further detail the configuration of FIG. 3 that enables movement along both X- and Y-axes. FIGS. 4A-B illustrate two opposing sides of the attachment element 210. (Note that some interior features of the attachment element are shown by a dashed line for reference.) FIGS. 5A-B illustrate two opposing sides of the first ring 252. FIGS. 6A-B illustrate two opposing sides of the second ring 254. As described previously, the screw 262 and the pin 266 are coupled to the first ring 252. However, the screw 262 is rotated within a threaded passageway 226 to cause movement of the screw 262 along the X-axis. Correspondingly, movement of the screw 262 causes movement of the first ring 252. As also described above, the screw 272 and the pin 276 also extend through the first ring 252 along the perpendicular Y-axis. Therefore, as can be seen from FIG. 3, when the ring 252 moves along the X-axis, the screw 272 and the pin 276 must also move transversely with the ring 252. The screw 272 and the pin 276 also extend through the attachment element 210 along the perpendicular Y-axis. If the attachment element 210 does not allow the screw 272 and the pin 276 to move along the X-axis, the first ring 252 is locked and cannot move. Accordingly, instead of impeding the movement of the screw 272 and the pin 276, the attachment element 210 accommodates movement of the screw 272 and the pin 276 along the X-axis. In particular, the screw passageway 286 has a width w parallel to the X-axis, allowing the screw 272 to move with the first ring 252. Similarly, as shown in FIG. 5B, the pin passageway 288 shown in FIG. 5B, the pin passageway 288 has a width w parallel to the X-axis, allowing the pin 276 to move with the ring 252 along the X-axis. The width w of both the screw passageway 286 and pin passageway 288 have a magnitude that is equal to or greater than the total distance that the ring 252 can travel within the central passageway 211. Although the shape of the screw passageway 286 and the pin passageway 288 shown in FIGS. 4A and 4B appear to be substantially rectangular, it is understood that the slot-like shapes may have other appropriate shape profiles, such as an oval, to facilitate manufacturing for example.

In general, the screw passageway 287 provides minimal resistance to the movement of the screw 272 along the Y-axis, but provides support to the screw 272 along the Z axis as shown in FIG. 4A. In some embodiments, bearings or similar guiding elements may be employed to facilitate movement of the screw 272 through the screw passageway 287. Unlike the screw 262, the screw 272 does not pass through a threaded passageway in the attachment element 210. Rather, the screw 272 passes through the threaded passageway 290 in the first ring 252. The head 273 of the screw 272 at the opening 287 of the screw passageway 286 can be rotated about the Y-axis, for example, by a screwdriver. Such action causes the threads of the screw 272 to act against the threads of the threaded passageway 290 and to move the screw 272 along the Y-axis. When turned in one direction, e.g. clockwise, the screw 272 moves further into the central passageway 211. When turned in the other direction, e.g. counterclockwise, the screw 272 moves outwardly away from the center of the annular attachment element 210. Because the screw 272 is attached to the second ring 254 at the screw-end cavity 258, the second ring 254 moves with the screw 272 along the Y-axis. The screw 272 engages the second ring 254 at the screw-end cavity 258 in a manner that allows the screw 272 to rotate freely within the screw-end cavity 258 while also allowing the screw 272 to cause the second ring 254 to move laterally with the screw 262. For example, as shown in FIG. 4, the screw 272 may have an enlarged end 274 which is received, e.g. snapped, into interlocking engagement with the screw-end cavity 258. It is contemplated that other embodiments may employ other techniques, such as a rivet-like attachment or the like, for coupling the screw 272 to the second ring 254. The screw 272 rotates freely within the screw passageway 286 of the attachment element 210.

The pin 276 extends through the pin passageway 288 of the attachment element 210 and the pin passageway 289 of the first ring 252 to provide further support for the second ring 254. When the screw 272 moves along the Y-axis within the threaded passageway 290 of the first ring 252, the pin 276 moves correspondingly within the pin passageway 288 and the pin passageway 289. The pin 266 is fixed to the pin-end cavity 259 of the second ring 254, so that it moves with the second ring 254 as the screw 272 moves the second ring 254 along Y-axis. Techniques for fixing the pin 266 to the first ring 252 may include, for example, welding, adhesive attachment, threaded engagement, interlocking engagement, frictional engagement, and the like. In some embodiments, the length of the pin 276 may cause the pin 276 in some positions to extend outwardly from the pin passageway 288. The pin 276 is not threaded and does not rotate as it moves. Rather the pin 276 slides through the pin passageways 288 and 289, which provide minimal resistance to the pin 276 along the Y-axis but support the pin 276 along the Z axis. In some embodiments, bearings or similar guiding elements may be employed to facilitate movement of the pin 276 through the pin passageways 288 and 286. Indeed, as shown in FIGS. 5B, 6B, and 7B, the pin 266 has a non-circular, hexagonal profile and the pin passageways 288 and 289 have a corresponding non-circular, rectangular profile. The flat surfaces on the top and bottom sides of the pin 276 and the pin passageways 288 and 289 provide resistance to any rotation that the screw 272 may impart to the ring 254 when the screw 272 is rotated about Y-axis.

In sum, operation of the screw 262 moves the first ring 252 and the second ring 254 laterally along the X-axis relative to the attachment element 210, while the screw 272 moves the second ring laterally along the Y-axis relative to the attachment element 210. Accordingly, the second ring 254 provides a translatable stage which can be moved relative to the attachment element 210 along both the X- and Y-axes. When the attachment element 210 is fixed to the eye surface 1A, the screws 262 and 272 can be operated to center the second ring 254 over the pupil 3 or other selected feature. Once the second ring 254 is properly aligned, the screws 262 and 272 prevent further movement and misalignment of the second ring 254.

A targeting device may be employed to guide the movement of the second ring 254. For example, as shown in FIG. 7A, after the attachment element 210 is fixed to the eye surface 1A, a targeting device 295 is positioned at the second ring 254 to present cross-hairs 296A, which identify the center of ring passageway 255 of the second ring 254 for the user. The targeting device 295 may be a disk that fits over or into the second ring 254. The cross-hairs 296A are positioned on a transparent or semi-transparent surface 297, such as glass or a clear plastic, so that a user can view both the cross-hairs 296A and the eye below the cross-hairs 296A. The user can then operate the screws 262 and 272 to move the second ring 254 and align the cross-hairs 296A over a the pupil 3, or other feature of the eye. Once the second ring 254 is properly aligned, the targeting device 295 may be removed and the applicator 110 may be positioned within the second ring 254. Other targeting devices may include other types of indicators such as a light-based indicator. As shown in FIG. 7B, other identifiers, such as a series of concentric circles 296B ("a bull's eye"), may be employed with the targeting device 295 instead of cross-hairs 296A.

As shown in FIG. 1, the second ring 254 acts as a coupling element and receives the applicator 110 coaxially through a ring passageway 255 into the selected position. When the applicator 110 is positioned within the second ring 254, the center of the applicator 110 corresponds with the center of the ring passageway 255 so that the user can predict where the energy from the energy conducting element 111 will be delivered. (This assumes that the energy conducting element 111 is centered at least at the distal end 110B of the applicator 110. If this is not the case, the positioning system 200 can advantageously be adjusted to account for any such offset.) Any coupling technique, such as a mechanical attachment, may be employed to keep the energy conducting element 111 stably positioned within the second ring 252. For example, as shown in FIG. 1, the applicator 110 may have one or more stops 112 that extend transversely from an outer surface of the applicator 110 and that abut or engage the second ring 254 when the applicator 110 moves through the ring passageway 255 to a desired position along the Z-axis. This position along the Z-axis determines the distance between the bottom surface 113 of the applicator 110 and the eye surface 1A. The stops 112 may also be adjustable so that the distance between the bottom surface 113 and the eye surface 1A may be varied if desired.

Figure 8:
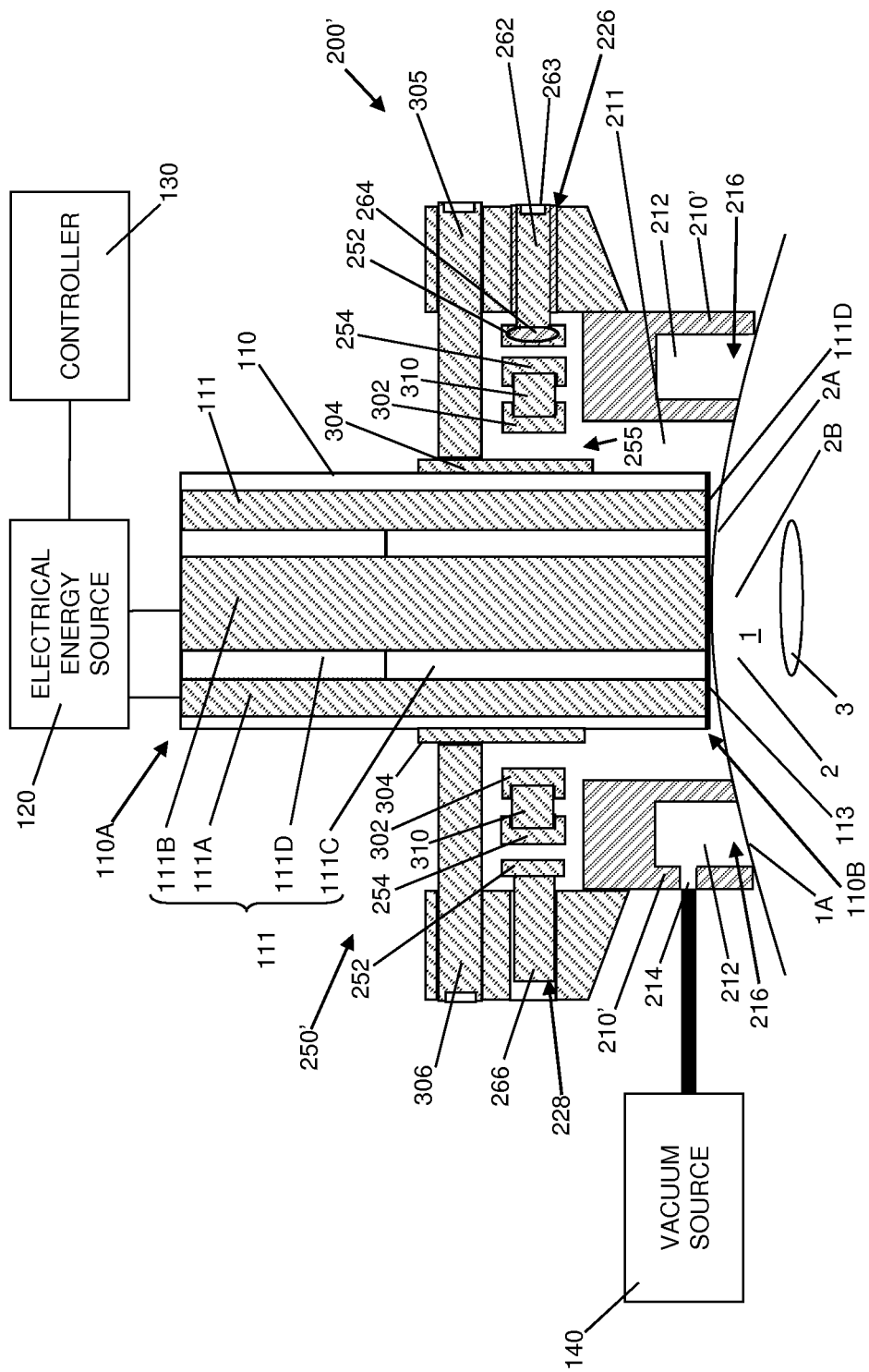
FIG. 8 illustrates another embodiment employing a positioning system that accurately positions an applicator to deliver energy to targeted areas of corneal fibrils in an eye.
Figure 9:
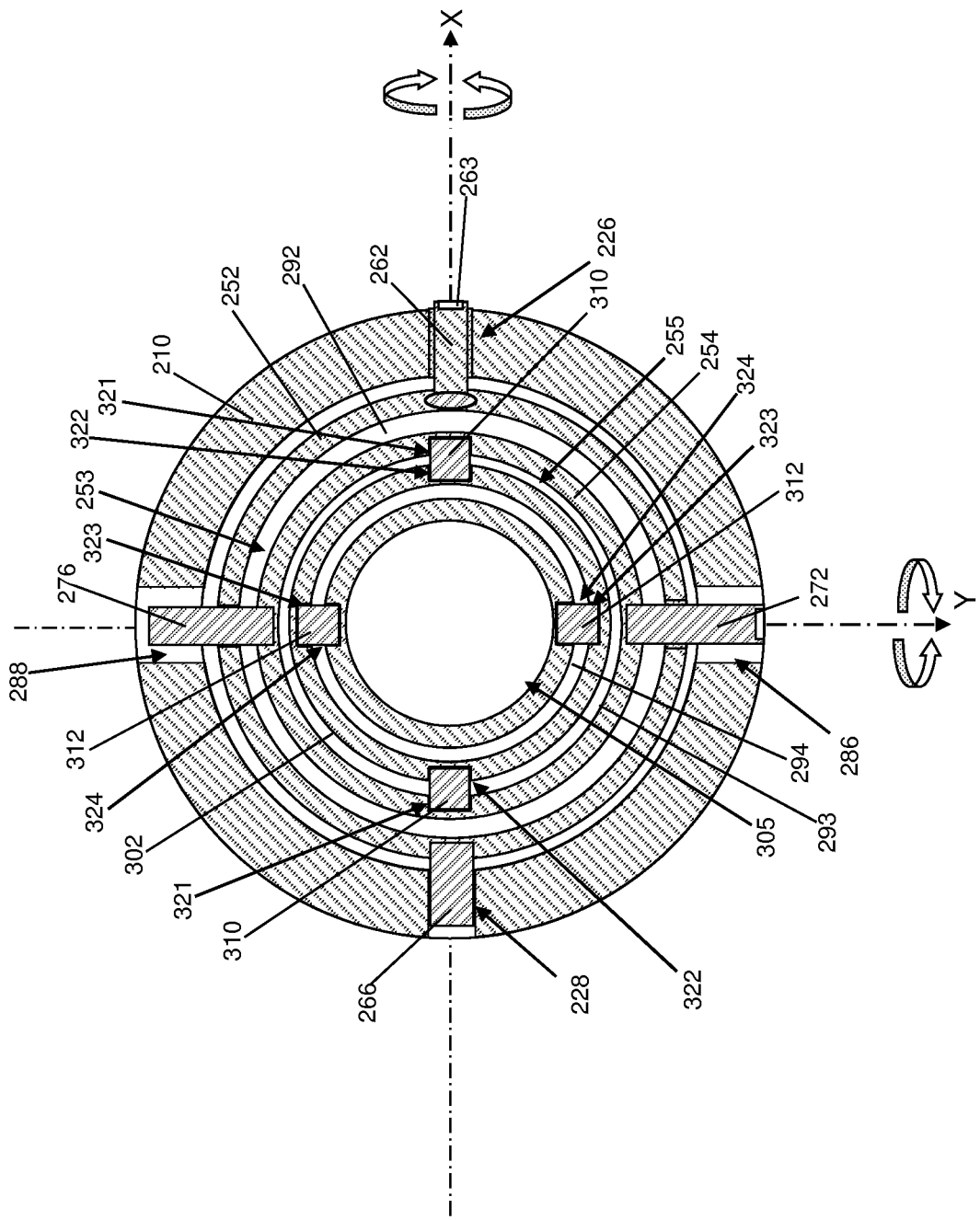
FIG. 9 illustrates a cross-sectional view of aspects of the embodiment of FIG. 8.
Figure 10:
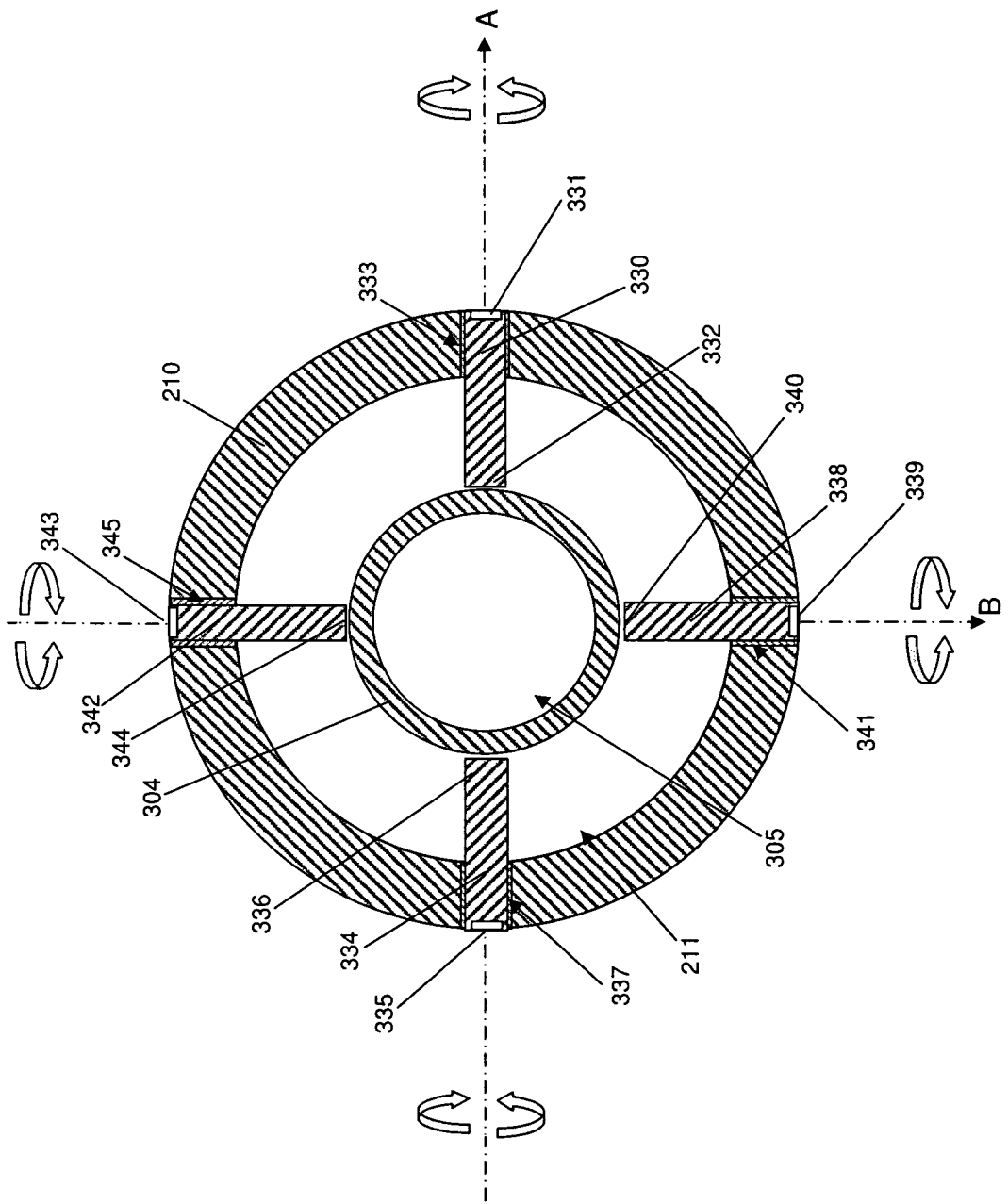
FIG. 10 illustrates a cross-sectional view of aspects of the embodiment of FIG. 8.

The embodiment of FIG. 1 provides a positioning system 200 that allows the position of the applicator 110 with respect to the attachment element 210 to be adjusted laterally along an X-Y plane. However, according to aspects of the present invention, other positioning systems may provide additional degrees of freedom. For example, FIGS. 8-10 illustrate a system with a positioning system 200'. In addition to allowing the position of the applicator 110 to be adjusted laterally along an X-Y plane, the positioning system 200' enables the position to be adjusted rotationally about the X- and Y-axes. As shown in FIG. 8, the positioning system 200' includes many of the same elements that are shown in the positioning system 200 of FIG. 1 and that permit lateral movement along the X- and Y-axes. (Except where otherwise indicated, elements with the same reference numerals are generally the same.) In particular, the screws 262 and 272 are operated to move the ring 254 to move about the X- and Y-axes. However, in the positioning system 200' of FIG. 8, an additional ring 302 as well as a cylinder, or substantially tube-like structure, 304 are disposed within the ring 254, i.e. in the ring passageway 255 of the second ring 254. The ring 302 rotates about the X-axis, while the cylinder 304 rotates about the Y-axis. Accordingly, the ring 302 and the cylinder 304 enable the positioning system 200' to adjust the position of the applicator 110 further by rotation about the X- and Y-axes. As described further below, the cylinder 304, rather than the ring 254, receives and correspondingly couples the applicator 110 to the receiving element 250'.

As FIG. 8 further illustrates, the attachment element 210' extends upwardly and outwardly to accommodate receiving element 250', which includes the rings 252, 254, and 302 as well as cylinder 304. FIG. 9 is a cross-sectional view illustrating further details on the rings 252, 254, and 302 as well as cylinder 304. In particular, FIG. 9 shows that two pins 310 couple the ring 302 to the ring 254, and two pins 312 couple the cylinder 304 to the ring 302. The pins 310 are received into pin cavities 321 in the ring 254 and into corresponding pin cavities 322 in the ring 302. The pins 310 are aligned with the X-axis and engage the cavities 321 and 322 in a manner that allows the pins 310 to rotate freely about the X-axis while preventing the pins 310 from moving laterally out of the cavities 321 and 322. For example, the pins 310 may have an enlarged end which is received, e.g. snapped, into interlocking engagement with the cavities 321 and 322. It is contemplated that other embodiments may employ other appropriate coupling techniques, such as a rivet-like attachment or the like. Similarly, the pins 312 are received into pin cavities 323 in the ring 302 and into corresponding pin cavities 324 in the cylinder 304. The pins 312 are aligned with the Y-axis and engage the cavities 323 and 324 in a manner that allows the pins 312 to rotate freely about the Y-axis while preventing the pins 310 from moving laterally out of the cavities 323 and 324. Accordingly, the pins 310 allow the ring 302 to rotate about the X-axis, and the pins 312 allow the cylinder 304 to rotate about the Y-axis. When the ring 302 rotates about the X-axis, the pins 312 which couple the ring 302 and the cylinder 304 cause the cylinder 304 to also rotate about the X-axis. It is noted that the annular gap 293 between the rings 254 and 302 and the annular gap 294 between the ring 302 and the cylinder 304 are dimensioned to permit rotation of the ring 302 and the cylinder 304.

As further illustrated in FIGS. 8 and 10, operation of screws 330, 334, 338, and 342 enable the ring 302 and the cylinder 304 to be rotated. Moreover, the screws 305 and 306 enable the rotation of the ring 302 and the cylinder 304 to be locked in place for the applicator 110. FIG. 10 is a cross-sectional view of the screws 330, 334, 338, and 342. The screws 330, 334, 338, and 342 are spaced from the X-Y plane, so that they can apply a torque about the X- and Y-axes and cause rotation of the ring 302 and cylinder 304 about these axes. As shown in 10, the axes in this separate plane are referred to as axes A and B. As shown in FIG. 10, the screws 330, 334, 338, and 342 extend through threaded passageways 333, 337, 341, and 345 in the attachment element 210, respectively. In addition, each of the ends 332, 336, 340, and 344 of the screws 330, 334, 338, and 342, respectively, abut the cylinder 304 which, as shown in FIG. 8, extends upwardly from the X-Y plane. Accordingly, a screwdriver, or similar tool, may be applied to the screw heads 331, 335, 339, and 343 to cause movement of the screws 330, 334, 338, and 342 through the threaded passageways 333, 337, 341, and 345, respectively. When one of the screws 330, 334, 338, and 342 abuts the cylinder 304, further movement of the screw toward the cylinder 304 applies a force to the cylinder 304, which in turn results in a torque about the X- or Y-axis. As FIG. 10 illustrates, movement of the screws 330 and 334 against the cylinder 304 applies forces along the A-axis. A force against the cylinder 304 along the A-axis produces a torque about the Y-axis. As the pins 312 permit free rotation of the cylinder 304 about the Y-axis, the cylinder 304 rotates when this torque is applied. As the forces from the screws 330 and 334 on the cylinder 304 are applied in opposing directions, the direction of rotation about the Y-axis depends on whether the screw 330 or the screw 334 applies the force. Meanwhile, the movement of the screws 338 and 342 against the cylinder 304 applies opposing forces along the B-axis. A force against the cylinder 304 along the B-axis produces a torque about the X-axis. The pins 312 do not permit rotation about the X-axis, but the pins 312 couple the cylinder 304 to the ring 302 which is permitted to rotate freely about the X-axis by the pins 310. As such, a force applied along the B-axis causes the ring 302 and the cylinder 304 rotate about the X-axis. As the forces from the screws 338 and 342 on the cylinder 304 are applied in opposing directions, the direction of rotation about the Y-axis depends on whether the screw 338 or the screw 338 applies the force. Accordingly, operation of the screws 330, 334, 338, and 342 enables angular position of the cylinder 304 with respect to the attachment element 210 to be adjusted. It is noted that the screws 330, 334, 338, and 342 are generally operated in sequence rather than simultaneously. To facilitate adjustment of the angular position, the user may employ a targeting device, as illustrated in FIG. 7, for example.

Furthermore, because the screws 330 and 334 apply opposing forces along the A-axis, once one of the screws 330 and 334 is used to adjust the angular position of the cylinder 304 about the Y-axis, the other screw can be tightened in opposition against the cylinder 304 to fix the selected angular position. Similarly, because the screws 338 and 342 apply opposing forces along the B-axis, once one of the screws 338 or 342 is used to adjust the angular position of the cylinder 304 about the X-axis, the other screw can be tightened in opposition against the cylinder 304 to fix the selected angular position. It is noted that applying the screws 330, 334, 338, and 342 against the cylinder 304 also locks the lateral position of the cylinder 304. Other embodiments may employ similar arrangement of screws to create a lock for the set position of the receiving element. As described previously, this lateral position is determined by operation of the screws 362 and 372.

Once the lateral and angular positions of the cylinder 304 have been set, the cylinder 304 can receive the applicator 110. The applicator 110 is thus accurately positioned for targeting selected areas of the cornea 2.

Accordingly, the example systems of FIGS. 1 and 8 illustrate how a positioning system may be employed to achieve more accurate positioning of an applicator for eye therapy. Variations of these systems are contemplated, however. For example, a positioning system according to aspects of the present invention may provide any combination of lateral or angular adjustments, e.g., lateral movement along the X- and/or Y-axes and/or rotation about the X- and/or Y-axes.

Figure 11:
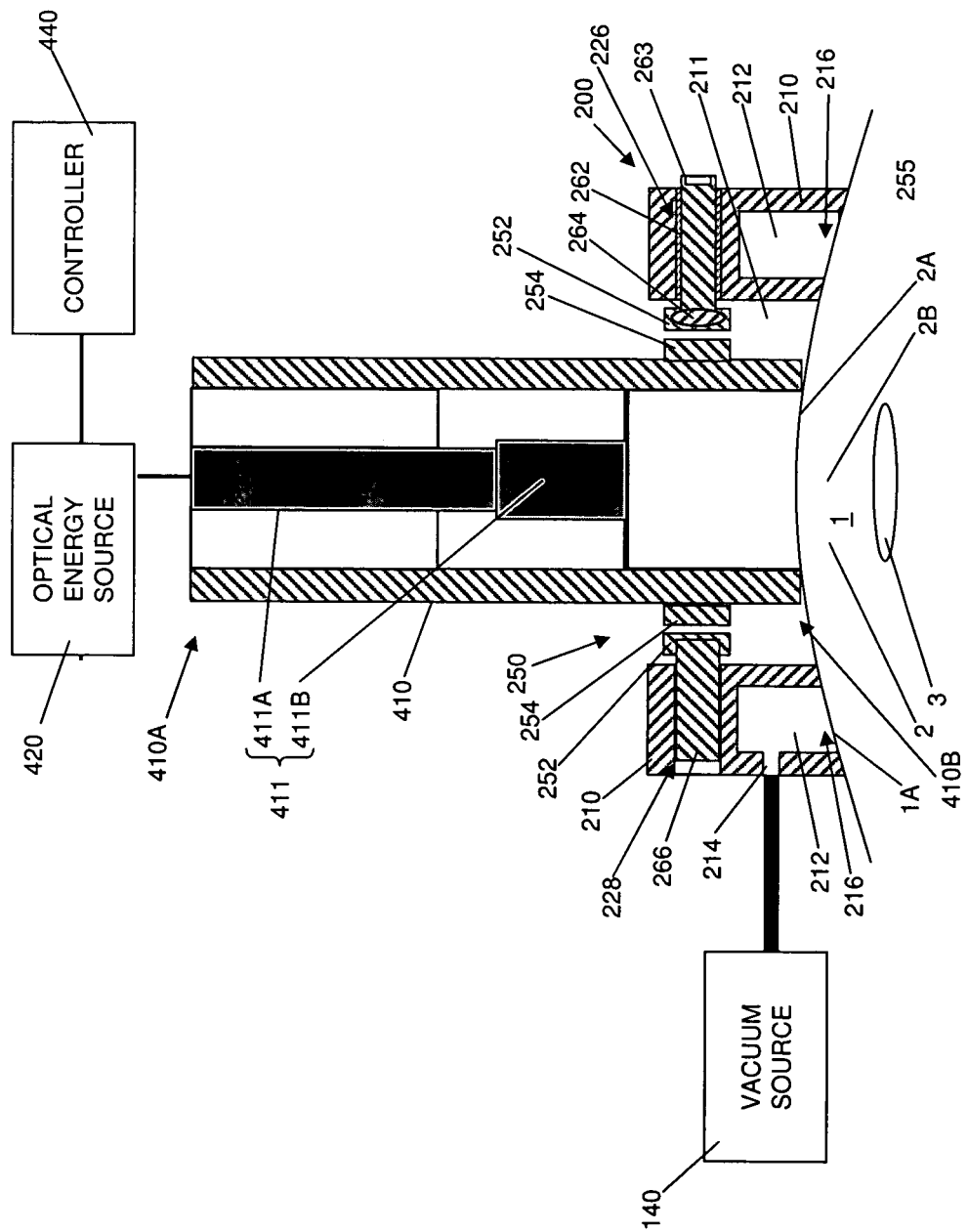
FIG. 11 illustrates yet another embodiment employing a positioning system that accurately positions an applicator for to deliver energy to targeted areas of corneal fibrils in an eye.

It is also contemplated that other systems may be employed to apply energy to cause reshaping of the cornea. As shown in FIG. 11, another embodiment of the present invention employs an applicator 410 that includes an optical energy conducting element 411. The positioning system 200 shown in FIG. 11 operates similarly to the corresponding system described with reference to FIG. 1. The optical energy conducting element 411 is operably connected to an optical energy source 420, for example, via conventional optical fiber. The optical energy source 420 may include a laser, a light emitting diode, or the like. The optical energy conducting element 411 extends to the distal end 410B from the proximal end 410A, where it is operably connected with the optical source 420. The optical energy conducting element includes an optical fiber 411A. Thus, the optical fiber 411A receives optical energy from the optical energy source 420 at the proximal end 410A and directs the optical energy to the distal end 410B, where the cornea 2 of an eye 1 is positioned. A controller 440 may be operably connected to the optical energy source 420 to control the delivery, e.g. timing, of the optical energy to the optical conducting element 411. The optical energy conducting element 411 irradiates the cornea 2 with the optical energy and delivers energy for appropriately shrinking collagen fibers in the mid-depth region 2B of the cornea 2. As also illustrated in FIG. 4, the optical conducting element may optionally include an optical focus element 211B, such as a lens, to focus the optical energy and to determine the pattern of irradiation for the cornea 2. As further illustrated in FIG. 4, the applicator 410 and the optical energy conducting element 411 are positioned over the cornea 2 by the positioning system 200 to deliver the optical energy to targeted areas of the cornea 2.

It further noted that although the applicator 110 in the examples above is a separate element received into the positioning systems 200 or 200', the applicator 110 and the positioning system may be combined to form a more integrated device.

It is additionally noted that although the adjustments in the examples above can be achieved by manually applying a tool, such as a screwdriver, aspects of the adjustments may be motorized or automated to further facilitate the adjustment process. Advantageously, automating the adjustment process facilitates making finer adjustments to achieve greater adjustment accuracy. In addition, such systems do not require the manual manipulation of small screws or the like. For example, as FIGS. 12A and 12B illustrate, embodiments may employ controllable adjustment systems 500 to adjust the receiving element 250. (Except where otherwise indicated, elements with the same reference numerals are generally the same.)

In FIG. 12A, the adjustment system 500 includes a motor 510 configured to drive one or more gears 520 that engage the screw 262. When the gears 520 are driven by the motor 510, the screw 262 rotates and moves laterally through the threaded passageway 226. The combination of gears 520 and screw 262 operate similarly to a worm-gear configuration. In this way, the position of the receiving element 250 along the X-axis can be adjusted as described above.

Alternatively, as shown in FIG. 12B, the adjustment system 500 includes an electrical source 550 configured to drive a piezoelectric element 540 that is coupled to a pin 262'. In response to a signal from the electrical source 550, the piezoelectric element 540 expands or contracts, causing the unthreaded pin 262' to move laterally in unthreaded passageway 226'. The pin 262' can be used in place of the screw 262 described previously, because operation of the piezoelectric element 540 directly results in lateral movement by the pin 262'. As such, the use of threaded components to cause rotation is not required. Moreover, the coupling between the piezoelectric element 540 and the pin 262' keeps the pin 262' in place after it has been adjusted. Accordingly, operation of the piezoelectric element 540 enables the position of the receiving element 250 along the X-axis.

As illustrated in FIGS. 12A and 12B, the adjustment systems 500 may include a user interface system 530 that accepts input from a user and correspondingly operates the adjustment system 500. The user interface system 340, for example, may be a device with a keypad to receive input from a user. The keypad may be part of a processing system, such as a conventional personal computer, with software to control the adjustment system 500. Alternatively, the user interface system 530 may be a device, such as a joystick, that receives instructions from the user through more electromechanically oriented input and sends corresponding signals for the operation of the adjustment system 500.

Of course, the adjustment systems 500 may be employed with other components of the systems described herein. For example, the adjustment system 500 may be applied to the screws 272, 330, 334, 338, and 342 described previously.

Additionally, it is further contemplated that although the attachment element 210 in the embodiments above is a vacuum ring which is auctioned to the eye surface, other types of attachment elements may be employed. For instance, the attachment element may be fixed to other portions of the head. Systems employing such attachment elements may also employ adjustable positioning systems according to aspects of the present invention.

Moreover, although the embodiments described previously may employ screws, other types of adjustable couplings may be employed. For example, instead of using a threaded device, a ratchet-type device or the like may be employed which determines positions according to set increments.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

It is also understood that the Figures provided in the present application are merely illustrative and serve to provide a clear understanding of the concepts described herein. The Figures are not "to scale" and do not limit embodiments to the specific configurations and spatial relationships illustrated therein. In addition, the elements shown in each Figure may omit some features of the illustrated embodiment for simplicity, but such omissions are not intended to limit the embodiment.

What is claimed is:

1. A system for aligning an eye therapy instrument over a feature of an eye, comprising:
    an eye therapy instrument;
    an attachment element configured to be removably attached to a surface of an eye, the attachment element having a first aperture defining a first passageway through the attachment element;
    a receiving element operably coupled to the attachment element and movable relative to the attachment element, the receiving element having a second aperture defining a second passageway through the receiving element, the first passageway and the second passageway being configured to provide access to a feature of an eye, the receiving element having a coupling element configured to operably couple the eye therapy instrument to the receiving element and adjustably position the eye therapy instrument with respect to the attachment element, the eye therapy instrument being disposed in the first passageway and the second passageway when the eye therapy instrument is coupled to the receiving element, the receiving element being movable along at least two axes relative to the attachment element when the receiving element is coupled to the attachment element; and
    a movement element coupling the receiving element and the attachment element and controlling the movement of the receiving element relative to the attachment element, wherein the movement element includes at least one screw engaging the receiving element, the at least one screw being adjustable to move the receiving element along a direction defined by the at least one screw.

2. The system according to claim 1, wherein the at least one screw includes two orthogonal screws, and the receiving element moves along a direction defined by each screw.

3. A system for aligning an eye therapy instrument over a feature of an eye, comprising:
    an eye therapy instrument;
    an attachment element configured to be removably attached to a surface of an eye, the attachment element having a first aperture defining a first passageway through the attachment element;
    a receiving element operably coupled to the attachment element and movable relative to the attachment element, the receiving element having a second aperture defining a second passageway through the receiving element, the first passageway and the second passageway being configured to provide access to a feature of an eye, the receiving element having a coupling element configured to operably couple the eye therapy instrument to the receiving element and adjustably position the eye therapy instrument with respect to the attachment element, the eye therapy instrument being disposed in the first passageway and the second passageway when the eye therapy instrument is coupled to the receiving element, the receiving element being movable along at least two axes relative to the attachment element when the receiving element is coupled to the attachment element; and
    a movement element coupling the receiving element and the attachment element and controlling the movement of the receiving element relative to the attachment element, wherein the movement element includes at least one axle engaging the receiving element, the receiving element being rotatable about an axis defined by the axle.

4. The system according to claim 3, wherein the at least one axle includes two orthogonal axles, and the receiving element is rotatable about axes defines by the two axles.

5. A method for aligning an eye therapy instrument over a feature of an eye, comprising:
    removably attaching a positioning system to a surface of an eye, the positioning system including:
        an attachment element configured to be removably attached to the surface of the eye, and
        a receiving element operably coupled to the attachment element and movable relative to the attachment element along at least two axes when the receiving element is coupled to the attachment element;
    removably attaching a targeting device to the receiving element;
    moving the targeting device and the receiving element relative to the attachment element to position the receiving element over a feature of the eye;
    in response to the receiving element being positioned over a feature of the eye, removing the targeting device from the receiving element; and
    in response to the targeting device being removed from the receiving element, coupling an eye therapy instrument to the receiving element.

6. The method according to claim 5, wherein the feature of the eye is a pupil and the step of moving the targeting device and the receiving element comprises centering the receiving element over the pupil.

7. The method according to claim 5, wherein the step of positioning a receiving element comprises moving the targeting device and the receiving element relative to a center of a pupil or an apex of a cornea.

8. The method according to claim 5, wherein the step of moving the targeting device and the receiving element includes operating an adjustment system, the adjustment system operably coupled to the receiving element and controlling movement of the receiving element relative to the attachment element.

9. The method according to claim 8, wherein the adjustment system includes a user-controllable electromechanical device.

10. The method according to claim 9, wherein the user-controllable electromechanical device is a joystick.

11. The method according to claim 5, wherein the targeting device includes an indicator for guiding movement of the receiving element over a feature of the eye.

12. The method according to claim 11, wherein the indicator comprises at least one of a cross-hairs and a series of concentric circles.

13. The method according to claim 5, wherein the removably attaching the positioning system to the surface of the eye includes attaching the attachment element to the surface of the eye and coupling the receiving element to the attachment element, and the removably attaching the targeting device to the receiving element is in response to the removably attaching the positioning system to the surface of the eye.

\* \* \* \* \*